US008334364B2

(12) United States Patent
Yamamoto et al.

(10) Patent No.: US 8,334,364 B2
(45) Date of Patent: *Dec. 18, 2012

(54) HIGH-MOLECULAR WEIGHT DERIVATIVE OF NUCLEIC ACID ANTIMETABOLITE

(75) Inventors: Keiichiro Yamamoto, Kita-ku (JP); Kazutoshi Takashio, Kita-ku (JP)

(73) Assignee: Nipon Kayaku Kabushiki Kaisha, Tokyo (JP)

( * ) Notice: Subject to any disclaimer, the term of this patent is extended or adjusted under 35 U.S.C. 154(b) by 532 days.

This patent is subject to a terminal disclaimer.

(21) Appl. No.: 12/312,009

(22) PCT Filed: Nov. 1, 2007

(86) PCT No.: PCT/JP2007/071305
§ 371 (c)(1),
(2), (4) Date: Jun. 22, 2009

(87) PCT Pub. No.: WO2008/056596
PCT Pub. Date: May 15, 2008

(65) Prior Publication Data
US 2009/0281300 A1 Nov. 12, 2009

(30) Foreign Application Priority Data

Nov. 6, 2006 (JP) ................................. 2006-300361

(51) Int. Cl.
C07K 5/093 (2006.01)
C07K 5/113 (2006.01)
C07K 7/06 (2006.01)
C07K 7/08 (2006.01)
C07H 19/06 (2006.01)
C07H 19/10 (2006.01)
C07H 19/067 (2006.01)
C07H 19/073 (2006.01)
C07H 19/09 (2006.01)
C07H 19/167 (2006.01)
C07H 19/173 (2006.01)
C07H 19/19 (2006.01)
C07H 19/20 (2006.01)

(52) U.S. Cl. .............. 530/332; 514/45; 514/46; 514/49; 514/50; 514/21.2; 514/21.3; 514/21.4; 514/21.6; 514/21.7; 514/21.8; 514/21.9; 536/27.23; 536/27.3; 536/27.6; 536/27.61; 536/27.62; 536/27.63; 536/27.81; 536/28.51; 536/28.53; 536/28.54; 536/28.55

(58) Field of Classification Search ........................ None
See application file for complete search history.

(56) References Cited

U.S. PATENT DOCUMENTS

| | | |
|---|---|---|
| 3,979,449 A | 9/1976 | Hirsbrunner et al. |
| 4,734,512 A | 3/1988 | Kaneko et al. |
| 4,892,733 A | 1/1990 | Bichon et al. |
| 5,037,883 A | 8/1991 | Kopecek et al. |
| 5,412,072 A | 5/1995 | Sakurai et al. ................ 530/322 |
| 5,438,072 A | 8/1995 | Bobee et al. |
| 5,552,517 A | 9/1996 | Martin |
| 5,571,889 A | 11/1996 | Katoh et al. .................. 528/328 |
| 5,614,549 A | 3/1997 | Greenwald et al. |
| 5,639,832 A | 6/1997 | Kroner et al. |
| 5,693,751 A | 12/1997 | Sakurai et al. |
| 5,877,205 A | 3/1999 | Andersson |
| 6,025,385 A | 2/2000 | Shimizu et al. |
| 6,153,655 A | 11/2000 | Martinez et al. |
| 6,262,107 B1 | 7/2001 | Li et al. |
| 6,322,817 B1 | 11/2001 | Maitra et al. |
| 6,376,470 B1 | 4/2002 | Greenwald et al. |
| 6,410,731 B2 | 6/2002 | Curran et al. |
| 6,458,347 B1 | 10/2002 | Sugawara et al. |
| 6,596,757 B1 | 7/2003 | Chari et al. |
| 6,713,454 B1 | 3/2004 | Ekwuribe et al. |
| 6,720,304 B1 | 4/2004 | Sinn et al. |
| 6,720,306 B2 | 4/2004 | Greenwald et al. |
| 6,858,582 B2 | 2/2005 | Yatvin et al. |
| 7,138,490 B2 | 11/2006 | Nakanishi et al. |
| 7,495,099 B2 | 2/2009 | Kitagawa et al. |
| 7,700,709 B2 | 4/2010 | Masuda et al. |
| 7,820,759 B2 | 10/2010 | Shimizu et al. |
| 8,188,222 B2 | 5/2012 | Yamamoto et al. |
| 2001/0003779 A1 | 6/2001 | Curran et al. |
| 2001/0014354 A1 | 8/2001 | Yokoyama et al. |
| 2001/0041189 A1 | 11/2001 | Xu |
| 2002/0016285 A1 | 2/2002 | Bhatt et al. ........................ 514/2 |

(Continued)

FOREIGN PATENT DOCUMENTS

CA 2 383 240 A1 3/2001

(Continued)

OTHER PUBLICATIONS

Final Rejection dated Jun. 8, 2011 in co-pending U.S. Appl. No. 11/662,834.

(Continued)

Primary Examiner — Eric S Olson
(74) Attorney, Agent, or Firm — Nields, Lemack & Frame, LLC

(57) ABSTRACT

[Problems] A derivative of a nucleic acid antimetabolite is demanded which can show a high therapeutic effect at a low dose.

[Means For Solving Problems] Disclosed is a high molecular weight derivative of a nucleic acid antimetabolite, which is characterized by comprising a high molecular weight compound comprising a polyethylene glycol moiety and a polymer moiety having a carboxyl group in a side chain and a nucleoside derivative which can act as a nucleic acid antimetabolite, wherein the carboxyl group in the side chain is bound to a hydroxyl group in the nucleoside derivative via an ester bond. Also disclosed is a method for producing the high molecular weight derivative.

13 Claims, 1 Drawing Sheet

U.S. PATENT DOCUMENTS

| | | | |
|---|---|---|---|
| 2002/0099013 A1 | 7/2002 | Piccariello et al. | 514/12 |
| 2002/0119951 A1 | 8/2002 | Seyedi et al. | |
| 2002/0161062 A1 | 10/2002 | Biermann et al. | |
| 2002/0183259 A1 | 12/2002 | Choe et al. | 514/19 |
| 2003/0032593 A1 | 2/2003 | Wender et al. | |
| 2003/0054977 A1 | 3/2003 | Kumar et al. | |
| 2003/0149003 A1 | 8/2003 | Chaplin et al. | |
| 2005/0119193 A1 | 6/2005 | Motoyama | |
| 2005/0147617 A1 | 7/2005 | Ji et al. | 424/178.1 |
| 2006/0057219 A1 | 3/2006 | Nagasaki et al. | |
| 2006/0067910 A1 | 3/2006 | Kitagawa et al. | 424/78.36 |
| 2006/0099265 A1 | 5/2006 | Shimizu et al. | |
| 2006/0233883 A1 | 10/2006 | Ishihara et al. | |
| 2007/0004674 A1 | 1/2007 | Shiotsu et al. | |
| 2007/0196497 A1 | 8/2007 | Pouliquen et al. | |
| 2008/0113028 A1 | 5/2008 | Shimizu et al. | |
| 2008/0145432 A1 | 6/2008 | Kakizawa et al. | |
| 2008/0221062 A1 | 9/2008 | Miyamoto et al. | |
| 2008/0269218 A1 | 10/2008 | Kuramochi et al. | |
| 2008/0280937 A1 | 11/2008 | Leamon et al. | |
| 2009/0012252 A1 | 1/2009 | Masuda et al. | |
| 2009/0162313 A1 | 6/2009 | Kitagawa et al. | |
| 2009/0239782 A1 | 9/2009 | Nakamura et al. | |
| 2009/0275732 A1 | 11/2009 | Hirotsu et al. | |
| 2010/0004403 A1 | 1/2010 | Kitagawa et al. | |
| 2010/0029849 A1 | 2/2010 | Yamamoto et al. | |
| 2010/0234537 A1 | 9/2010 | Kitagawa et al. | |
| 2010/0292414 A1 | 11/2010 | Kitagawa et al. | |
| 2011/0201754 A1 | 8/2011 | Kitagawa et al. | |
| 2011/0294980 A1 | 12/2011 | Nakanishi et al. | |
| 2012/0116051 A1 | 5/2012 | Kitagawa et al. | |

FOREIGN PATENT DOCUMENTS

| | | |
|---|---|---|
| CA | 2 334 615 A1 | 8/2001 |
| CN | 1307866 A | 8/2001 |
| CN | 1708540 A | 12/2005 |
| EP | 9 397 397 A2 | 11/1990 |
| EP | 0 583 955 A2 | 2/1994 |
| EP | 0 757 049 A1 | 2/1997 |
| EP | 1 127 570 A2 | 8/2001 |
| EP | 1 857 446 A1 | 11/2007 |
| JP | 61-243026 A | 10/1986 |
| JP | 62-96088 A | 5/1987 |
| JP | 62-145093 A | 6/1987 |
| JP | 63-10789 A | 1/1988 |
| JP | 63-23884 A | 2/1988 |
| JP | 63-502037 A | 8/1988 |
| JP | 64-61422 A | 3/1989 |
| JP | 64-61423 A | 3/1989 |
| JP | 2-300133 | 12/1990 |
| JP | 5-955 | 1/1993 |
| JP | 5-117385 A | 5/1993 |
| JP | 6-107565 A | 4/1994 |
| JP | 6-206815 A | 7/1994 |
| JP | 6-206830 A | 7/1994 |
| JP | 6-206832 | 7/1994 |
| JP | 6-296088 A | 10/1994 |
| JP | 6-310789 A | 11/1994 |
| JP | 6-323884 A | 11/1994 |
| JP | 8-48766 | 2/1996 |
| JP | 8-503689 A | 4/1996 |
| JP | 8-507558 A | 8/1996 |
| JP | 8-310970 A | 11/1996 |
| JP | 2694923 | 9/1997 |
| JP | 10-513187 A | 12/1998 |
| JP | 11-335267 A | 12/1999 |
| JP | 2000-515132 A | 11/2000 |
| JP | 2000-516948 A | 12/2000 |
| JP | 2000-517304 A | 12/2000 |
| JP | 2001-226294 A | 8/2001 |
| JP | 3268913 | 1/2002 |
| JP | 2002-69184 A | 3/2002 |
| JP | 2002-508400 A | 3/2002 |
| JP | 2002-512265 A | 4/2002 |
| JP | 3310000 A | 5/2002 |
| JP | 2003-509385 A | 3/2003 |
| JP | 2003-509386 A | 3/2003 |
| JP | 2003-511349 A | 3/2003 |
| JP | 2003-511423 A | 3/2003 |
| JP | 2003-524028 | 8/2003 |
| JP | 2003-525238 A | 8/2003 |
| JP | 2003-527443 | 9/2003 |
| JP | 2003-342167 A | 12/2003 |
| JP | 2003-342168 A | 12/2003 |
| JP | 2003-342269 A | 12/2003 |
| JP | 2004-39869 A | 2/2004 |
| JP | 2004-530736 A | 10/2004 |
| JP | 2004-532289 | 10/2004 |
| JP | 2005-507912 A | 3/2005 |
| JP | 2005-508832 A | 4/2005 |
| JP | 2005-517675 A | 6/2005 |
| JP | 2005-519122 | 6/2005 |
| JP | 2005-533026 A | 11/2005 |
| JP | 2006-510627 A | 3/2006 |
| JP | 2006-511571 A | 4/2006 |
| JP | 2006-120914 A | 5/2006 |
| JP | 2006-517572 A | 7/2006 |
| JP | 2006-524673 A | 11/2006 |
| JP | 2007-111211 A | 5/2007 |
| JP | 2007-511586 A | 5/2007 |
| JP | 2008-41610 A | 2/2008 |
| JP | 2006-521367 A | 10/2010 |
| WO | 93/24476 A | 12/1993 |
| WO | 96/23794 A | 8/1996 |
| WO | 97/38727 A | 10/1997 |
| WO | 98/02426 A | 1/1998 |
| WO | 98/07713 A | 2/1998 |
| WO | 98/08489 A1 | 3/1998 |
| WO | 99/53951 A | 10/1999 |
| WO | 01/19361 A2 | 3/2001 |
| WO | 01/19406 A2 | 3/2001 |
| WO | 01/19407 A2 | 3/2001 |
| WO | 01/26693 A2 | 4/2001 |
| WO | 01/64198 A2 | 9/2001 |
| WO | 01/70275 A2 | 9/2001 |
| WO | 01/92584 A1 | 12/2001 |
| WO | 02/06279 A1 | 1/2002 |
| WO | 02/065986 A2 | 8/2002 |
| WO | 02/065988 A2 | 8/2002 |
| WO | 02/066066 A1 | 8/2002 |
| WO | 03/000771 A1 | 1/2003 |
| WO | 03/035008 A2 | 5/2003 |
| WO | 03/055860 A1 | 7/2003 |
| WO | 2004/039869 | 5/2004 |
| WO | 2004/050087 A1 | 6/2004 |
| WO | 2004/056782 A1 | 7/2004 |
| WO | 2004/072051 A1 | 8/2004 |
| WO | 2004/082718 A1 | 9/2004 |
| WO | 2004/096212 A1 | 11/2004 |
| WO | 2005/000300 A1 | 1/2005 |
| WO | 2005/018674 A1 | 3/2005 |
| WO | 2005/066214 A1 | 7/2005 |
| WO | 2006/055760 A1 | 5/2006 |
| WO | 2006/095668 A1 | 9/2006 |
| WO | 2006/095783 A1 | 9/2006 |
| WO | 2006/115293 A1 | 11/2006 |
| WO | 2006/120914 | 11/2006 |
| WO | 2007/022493 A2 | 2/2007 |
| WO | 2007/080898 A1 | 7/2007 |
| WO | 2007/111211 | 10/2007 |
| WO | 2007/135910 A1 | 11/2007 |
| WO | 2008/010463 A1 | 1/2008 |
| WO | 2008/041610 | 4/2008 |
| WO | 2008/056596 A1 | 5/2008 |
| WO | 2008/056654 A1 | 5/2008 |

OTHER PUBLICATIONS

Office Action dated Jun. 16, 2011 in co-pending U.S. Appl. No. 12/225,230.

Final Rejection dated Jul. 27, 2011 in co-pending U.S. Appl. No. 12/311,086.

Russian Communication, with English translation, dated May 16, 2011 in co-pending foreign patent application No. RU 2008149932/04.

International Search Report dated Dec. 24, 2003 in U.S. patent 7,495,099 (PCT/JP03/13838).
Taiwanese communication dated Nov. 30, 2006 in U.S. patent 7,495,099 (TW092130275).
Russian communication dated Apr. 20, 2007 in U.S. patent 7,495,099 (RU2005116309/04).
European communication dated Sep. 25, 2008 in U.S. patent 7495099 (EP03769949.3).
International Search Report dated May 11, 2004 in co-pending U.S. Appl. No. 10/548,998 (PCT/JP2004/003647).
Chinese communication dated Oct. 20, 2006 in co-pending U.S. Appl. No. 10/548,998 (CN200480007329.5).
Russian communication dated Jun. 27, 2007 in co-pending U.S. Appl. No. 10/548,998 (RU2005132309/04).
European communication dated Feb. 17, 2009 in co-pending U.S. Appl. No. 10/548,998 (EP04721673.4).
Chinese communication dated Apr. 17, 2009 in co-pending U.S. Appl. No. 10/548,998 (CN200480007329.5).
European communication dated Jun. 5, 2009 in co-pending U.S. Appl. No. 10/548,998 (EP04721673.4).
International Search Report dated Nov. 15, 2005 in co-pending U.S. Appl. No. 12/322,322 (PCT/JP2005/017127).
International Search Report dated Jul. 25, 2006 in U.S. Patent 7,700,709 (PCT/JP2006/308826).
International Search Report dated May 15, 2007 in co-pending U.S. Appl. No. 12/225,230 (PCT/JP2007/055809).
International Search Report dated Aug. 21, 2007 in co-pending U.S. Appl. No. 12/226,962 (PCT/JP2007/060026).
European communication dated Oct. 23, 2009 in co-pending U.S. Appl. No. 12/226.962 (EP07743461.1).
International Search Report dated Oct. 16, 2007 in co-pending U.S. Appl. No. 12/309,061 (PCT/JP2007/063990).
International Search Report dated Jan. 8, 2008 in co-pending U.S. Appl. No. 12/311,086 (PCT/JP2007/068841).
Office Actions dated Jan. 21, 2009, Apr. 17, 2009, Jul. 10, 2009, Mar. 4, 2010 in co-pending U.S. Appl. No. 10/548,998.
Office Actions dated Oct. 19, 2009, Mar. 19, 2010, Jun. 23, 2010, Jul. 7, 2010 in co-pending U.S. Appl. No. 12/322,322.
Office Action dated Aug. 24, 2010 in co-pending U.S. Appl. No. 11/662,834.
Office Actions dated Jul. 21, 2010 in co-pending U.S. Appl. No. 12/309,061.
A.V. Shur, "High-Molecular Weight Compounds"; Course for Universities, Third Edition, Revised and supplemented, "Visshaja Shkola" Publishing House, 1981, 656 pages, see p. 265).
Chemical Abstracts, 6001, vol. 132; Oct. 10, 2000 No. 2—XP-002168038, (2000).
Merriam-Webster's Collegiate Dictionary—Eleventh Edition 2004.
J. Org. Chem. 2001, 66, 8135-8138; Keirs Gaukroger, et al.; "Novel Synthesis of Cis and Trans Isomers of Combretastatin A-4".
Anti-Cancer Drug Design; vol. 14, No. 6, Dec. 1999—ISSN 0266-9536.
Journal of Pharmaceutical Sciences, vol. 92, No. 7, Jul. 2003; Monica L. Adams et al.; "MiniReview—Amphiphilic Block Copolymers for Drug Delivery".
Chemistry and Biology, vol. 11, 787-797, Jun. 2004; Maria Vilenchick et al.; "Targeting Wide-Range Oncogenic Transformation via PU24FCI, a specific Inhibitor of Tumor Hsp90".
Trends in Molecular Medicine vol. 8, No. 4 (Suppl.) 2002; Len Neckers; "Hsp90 inhibitors as novel cancer chemotherapeutic agents".
Current Cancer Drug Targets, 2003, 3, 385-390; Udai Banerji et al.; "The Clinical Applications of Heat Shock Protein Inhibitors in Cancer Present and Future".
Journal of Pharmacokinetics and Biopharmaceutics, vol. 23, No. 4, 1995; Claudia S. Leopold; In vivo Pharmacokinetic Study for the Assessment of Poly(L-Aspartic Acid) as a Drug Carrier for Colon-Specific Drug Delivery).
International Search Report dated Dec. 9, 2008 in co-pending U.S. Appl. No. 12/678,620 (PCT/JP2008/067413).
Office Action dated Oct. 12, 2011 in co-pending U.S. Appl. No. 12/312,157.

Cancer Sci; Feb. 2004; vol. 95; No. 2;pp. 105-111; Akira Matsuda et al.; "Antitumor Activity of Sugar-Modified Cytosine Nucleosides".
Cancer Research 44, pp. 25-30, Jan. 1984; Yoshinori Kato et al.; "Antitumor Activity of 1-β-D-Arabinofuranosylcytosine conjugated With Polyglutamic Acid and Its Derivative".
Journal of Controlled Release 79 (2002) p. 55-70; Yun H. Choe et al.; "Anticancer drug delivery systems: multi-loaded N4-acyl poly(ethylene glycol) prodrugs of ara-C. II. Efficacy in ascites and solid tumors".
Office Action dated Sep. 9, 2011 in co-pending U.S. Appl. No. 12/226,962.
Colloids and Surfaces B: Biointerfaces V. 16 (1999) pp. 217-226, "Micelle-like structures of poly(ethyleneoxide)-block-poly(2-hydroxyethyl aspartamide)-methotrexate conjugates", Li, et al.
Pharmaceutical Research, V. 17, No. 5 (2000), pp. 607-611, "Methotrexate Esters of Poly (EthyleneOxide)-Block-Poly (2-Hydroxyethyl-L-Aspartamide). Part I: Effects of the Level of Methotrexate Conjugation on the Stability of Micelles and on Drug Release", Li, et al.
International Search Report dated Jul. 21, 2009 in co-pending international patent application No. PCT/JP2009/058325.
Taiwan Communication, with English translation, dated Jul. 22, 2011 in co-pending Taiwan Patent Application No. 094132581.
Advanced Drug Delivery Reviews 20 (1996) 1995-201; K. Yokoyama et al; "Limethason as a lipid microsphere preparation: An overview".
Chinese Office Action dated Nov. 10, 2010 in co-pending U.S. Appl. No. 12/309,061, filed Mar. 3, 2009 / Foreign Application No. 200780027210.8
Korean Office Action dated Nov. 8, 2010 in co-pending U.S. Appl. No. 10/548,998, filed Oct. 31, 2005 /Foreign Application No. 10-2005-7017245.
Bioorganic & Medicinal Chemistry Letters 15 (2005) pp. 3338-3343. "This identification, synthesis, protein crystal structure and in vitro biochemical evaluation of a new 3,4-diarylpyrazole class of Hsp90 inhibitors", Cheung, et al.
Molecular Cancer Therapeutics, 2006, 5(6), Jun. 2006, pp. 1628-1637, "Preclinical pharmacokinetics and metabolism of a novel diaryl pyrazole resorcinol series of heat shock protein 90 inhibitors", Smith, et al.
Registry Entry for Registry No. 171009-07-7, which entered STN on Dec. 6th, 1995, 3 pages.
Registry Entry for Registry No. 7689-03-4, which entered Stn on Nov. 16th, 1984, 3 pages.
Merriam-Webster Online Dictionary entry for "Derivative", (http://www.merriam-webster.com/dictionary/derivative), last accessed Feb. 9, 2011, 3 pages.
Office Action dated Apr. 4, 2011 in co-pending U.S. Appl. No. 12/311,086.
Final Rejection dated Feb. 28, 2011 in co-pending U.S. Appl. No. 12/309,061.
Chinese communication dated Aug. 11, 2010 in a co-pending foreign application.
Office action dated Nov. 12, 2010 in a co-pending U.S. Appl. No. 11/662,834.
Journal of Peptide Science, vol. 3, 141-144 (1997); Jan Izdebski et al.; "Evaluation of Carbodiimides Using a Competition Method".
Chinese Communication, with English translation, dated Oct. 10, 2011 in co-pending Chinese Patent Application No. 200880109404.7.
Office Action dated Dec. 15, 2011 in co-pending U.S. Appl. No. 11/662,834.
Final Rejection mailed Nov. 8, 2011 in co-pending U.S. Appl. No. 12/225,230.
Chinese Communication, with English translation, dated Sep. 23, 2011 in co-pending Chinese patent application No. 2007800177809.
Journal of Controlled Release, 2001, V. 74, No. 1-3, pp. 295-302, paragraph of "2. Structure of NK911", "Development of the polymer micelle carrier system for doxorubicin", Nakanishi, et al.
International Search Report mailed Jun. 23, 2009 in co-pending PCT application No. PCT/JP2009/055115.
Chinese Communication, with English translation, dated Aug. 31, 2011 in co-pending Chinese patent application No. 200980110087.5.

European Communication, dated Oct. 28, 2011 in co-pending European Patent Application No. EP 05783310.5.
Australian Communication, dated Oct. 28, 2011 in co-pending Australian Patent Application No. 2007252678.
Taiwanese Communication, with English translation, dated Dec. 14, 2011 in co-pending Taiwanese Application No. 094132581.
International Search Report dated Aug. 10, 2010 in co-pending PCT application No. PCT/JP2010/058034.
Final Rejection dated Feb. 16, 2012 in co-pending U.S. Appl. No. 12/226,962.
Notice of Allowance dated Mar. 1, 2012 in co-pending U.S. Appl. No. 12/312,157.
Office Action mailed Apr. 6, 2012 in co-pending U.S. Appl. No. 12/225,230.
Miscellaneous Communication mailed Mar. 19, 2012 in co-pending U.S. Appl. No. 12/312,157.
Office Action mailed Apr. 25, 2012 in co-pending U.S. Appl. No. 12/678,620.
Office Action-Restriction-mailed Apr. 27, 2012 in co-pending U.S. Appl. No. 12/922,747.
European Communication mailed Jan. 27, 2012 in corresponding European Patent Application No. 07831039.8.
Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.
Office Action mailed Jul. 30, 2012 in co-pending U.S. Appl. No. 12/922,747.
Final Rejection mailed Aug. 21, 2012 in co-pending U.S. Appl. No. 11/662,834.
Office Action mailed Aug. 22, 2012 in co-pending U.S. Appl. No. 12/991,041.
Notice of Allowance mailed Aug. 28, 2012 in co-pending U.S. Appl. No. 12/225,230.
Final Rejection mailed Oct. 17, 2012 in co-pending U.S. Appl. No. 12/678,620.

HIGH-MOLECULAR WEIGHT DERIVATIVE OF NUCLEIC ACID ANTIMETABOLITE

This application is the national stage (§371) of PCT/JP2007/071305, filed Nov. 1, 2007, which claims priority of JP2006-300361, filed Nov. 6, 2006.

TECHNICAL FIELD

The present invention relates to a high molecular weight derivative of a nucleic acid antimetabolite, the use of the same, and a method for manufacturing the same.

BACKGROUND ART

For the purpose of treating malignant tumors or viral diseases, various nucleic acid antimetabolites has been developed, and cytarabine, gemcitabine, doxifluridine, azacitidine, decitabine, nelarabine and the like as antitumor agents (anticancer agents), and zalcitabine, lamivudine and the like as antiviral agents are clinically used.

However, even though these nucleic acid antimetabolites exhibit strong in vitro activity, many of the antimetabolites cannot sufficiently exhibit the efficacy inherently possessed by the drugs or need to be administered in large amounts, owing to their susceptibility to in vivo metabolism and excretion. For example, gemcitabine has a strong in vitro cell growth inhibitory activity which is comparable to that of anticancer agents such as paclitaxel or doxorubicin, while in clinical practice, gemcitabine requires a high dose of 1000 mg/m$^2$ of the body surface area per administration. This is believed to be because the in vivo bioavailability is decreased as the amino group at the 4-position of the base is metabolized/deactivated by a cytidine deaminase, which is a 2'-deoxycytidine metabolizing enzyme (Non-Patent Document 1).

In some cases, binding of a drug to a polymer results in an improvement in the pharmacokinetics in vivo, and thus leading to an enhancement of the therapeutic effect. Non-Patent Document 2 describes a high molecular weight derivative in which a polyglutamic acid having an average molecular weight of about 30,000 is conjugated with cytarabine. However, such high molecular weight derivatives of drugs often induce hypersensitivity due to immune responses, and in that cases, the high molecular weight derivatives as a drug cannot be administered repeatedly.

Patent Document 1 describes a high molecular weight derivative in which a cytidine derivative is bound to a polyethylene glycol, and Non-Patent Document 3 describes a high molecular weight derivative in which both ends of the chain of a polyethylene glycol are substituted with aspartic acid in a branched form, and cytarabine is bound thereto. Furthermore, Patent Document 5 describes a high molecular weight derivative having a structure in which the ends of a polyethylene glycol chain are branched by using amino acids, and each of the branches releases drug after being subjected to a benzyl elimination reaction. However, for all of these high molecular weight derivatives, the rate of hydrolysis in the plasma is several tens of hours at the most, that is, the rate is not so much slowed, and the high molecular weight derivatives themselves do remain in vivo for a long time and do not release the included compounds over a long time. Furthermore, since these high molecular weight derivatives have large differences between the rate of hydrolysis in phosphate buffered physiological saline (PBS) and the rate of hydrolysis in the blood plasma, and the hydrolysis reaction depends largely on the enzymes in vivo, it is possible that the therapeutic effects in the clinical practice may be greatly affected by the individual differences of patients.

Patent Document 2 states that molecules in which a drug is bound to a block type polymer having a polyethylene glycol condensed with polyaspartic acid, form micelles and serve as a medicine. Furthermore, Patent Document 3 describes a high molecular weight molecule in which an anticancerous substance is bound to a carboxyl group in the glutamic acid side chain of a block type polymer having a polyethylene glycol condensed with polyglutamic acid. However, there is no description with regard to these high molecular weight derivatives using a nucleic acid antimetabolite as the drug binding thereto.

In addition, Patent Document 4 states that a water-soluble high molecular weight derivative in which a carboxyl group of a polymer of polyethylene glycol and polycarboxylic acid is linked to a phenolic hydroxyl group of a phenolic camptothecin by ester condensation, is suitable for cancer chemotherapy. However, the mode of binding of the drug in this molecule is an ester formed by phenol group bound to a carboxyl group, and this is not an ester formed by a primary alcohol or secondary alcohol bound to a carboxyl group. Also, no description is provided with regard to this high molecular weight derivative using a nucleic acid antimetabolite as the drug binding thereto.

Patent Document 1: Japanese Patent Application Laid-open Publication (Kohyo) No. 2003-524028

Patent Document 2: Japanese Patent No. 2694923

Patent Document 3: Japanese Patent Application Laid-open Publication (Kokai) No. 5-955

Patent Document 4: WO 2004/039869

Patent Document 5: Japanese Patent Application Laid-open Publication (Kohyo) No. 2004-532289

Non-Patent Document 1: Cancer Science, Japanese Cancer Association, Vol. 95, pp. 105-111 (2004)

Non-Patent Document 2: Cancer Research, American Association for Cancer Research, Vol. 44, pp. 25-30 (1984)

Non-Patent Document 3: Journal of Controlled Release, Elsevier, Vol. 79, pp. 55-70 (2002)

DISCLOSURE OF THE INVENTION

Problems to be Solved by the Invention

It is an object of the present invention to provide a nucleic acid antimetabolite which has superior effects at a lower dose and serves as a novel anticancer agent or antiviral agent.

Means for Solving the Problems

The inventors of the present invention devotedly conducted research to address the above-described problems, and as a result, found a high molecular weight derivative of a nucleic acid antimetabolite, specifically a high molecular weight derivative in which a carboxyl group in the side chain of a high molecular weight compound comprising a polyethylene glycol moiety and a polymer moiety having a carboxyl group in the side chain is linked to a hydroxyl group of a nucleic acid antimetabolite via an ester linkage.

Specifically, the present invention relates to the following (1) to (16).

(1) A high molecular weight derivative of a nucleic acid antimetabolite, in which a carboxyl group in the side chain of a high molecular weight compound comprising a polyethyleneglycol moiety and a polymer moiety having a carboxyl group in the side chain is linked to a hydroxyl group of a nucleic acid antimetabolite via an ester linkage.

(2) The high molecular weight derivative of a nucleic acid antimetabolite according to (1) above, wherein the polymer moiety having a carboxyl group in the side chain is a polyglutamic acid derivative.

(3) The high molecular weight derivative of a nucleic acid antimetabolite according to (1) or (2) above, wherein the high molecular weight derivative of a nucleic acid antimetabolite is represented by the following formula (1):

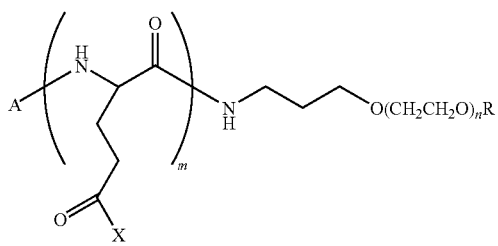

(1)

wherein R represents a hydrogen atom or a C1-C6 alkyl group; A represents a hydrogen atom, a C1-C6 acyl group or a C1-C6 alkoxycarbonyl group; m represents from 3 to 200 as an average value; n represents from 5 to 2000 as an average value; and X represents a group selected from the group consisting of a nucleic acid antimetabolite residue, a hydroxyl group, a hydrophobic substituent, and —N(R1)CONH(R2) wherein R1 and R2 may be identical or different and are each a C1-C6 alkyl group which may be substituted with a tertiary amino group, and X includes a nucleic acid antimetabolite residue and —N(R1)CONH(R2).

(4) The high molecular weight derivative of a nucleic acid antimetabolite according to (3) above, wherein, among m units, 5 to 95% have a nucleic acid antimetabolite residue for X, 0 to 95% have a hydroxyl group for X, 0 to 80% have a hydrophobic substituent for X, and 5 to 80% have —N(R1)CONH(R2) for X.

(5) The high molecular weight derivative of a nucleic acid antimetabolite according to (3) above, wherein among m units, 5 to 70% have a nucleic acid antimetabolite residue for X, 5 to 70% have a hydroxyl group for X, 20 to 70% have a hydrophobic substituent for X, and 5 to 70% have —N(R1)CONH(R2) for X.

(6) The high molecular weight derivative of a nucleic acid antimetabolite according to anyone of (3) to (5) above, wherein R is a C1-C4 alkyl group, A is a C2-C4 acyl group, m is from 5 to 100 as an average value, n is from 50 to 1000 as an average value, and the nucleic acid antimetabolite residue is any one of the nucleic acid antimetabolite residues represented by the following formula (2):

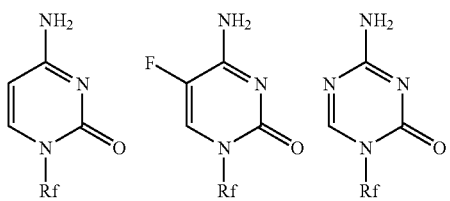

(2)

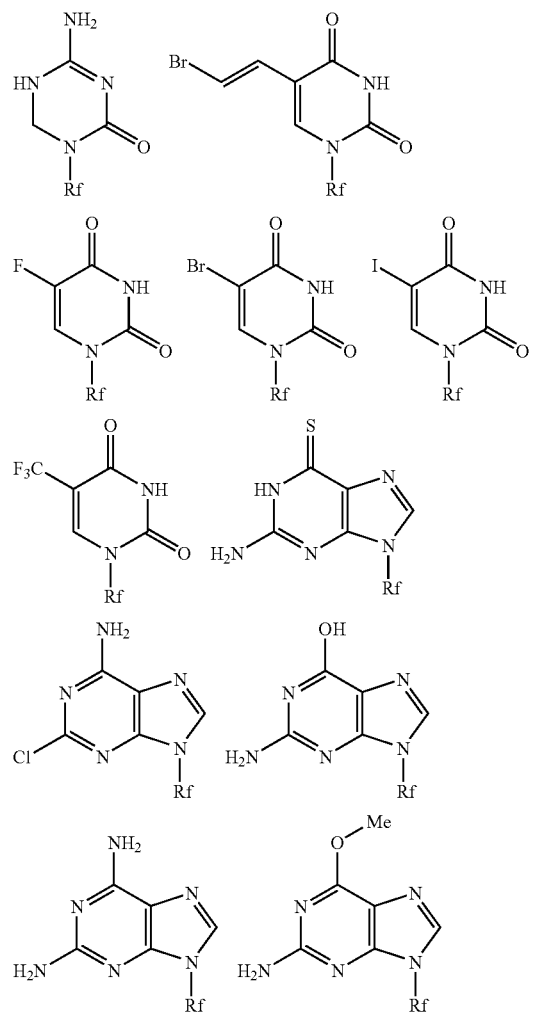

wherein —Rf represents a group selected from the group of substituents of formula (3):

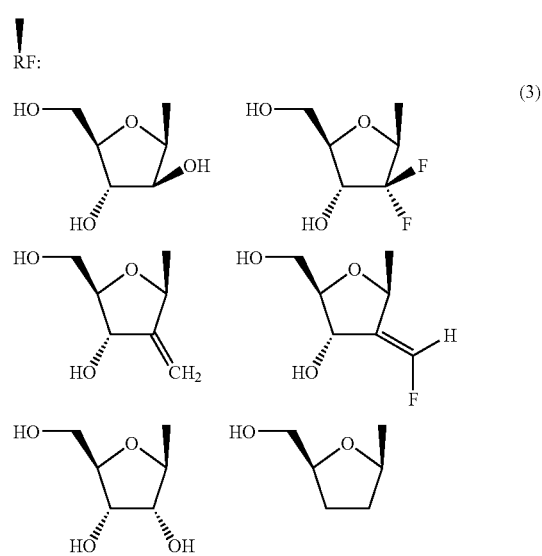

(3)

-continued

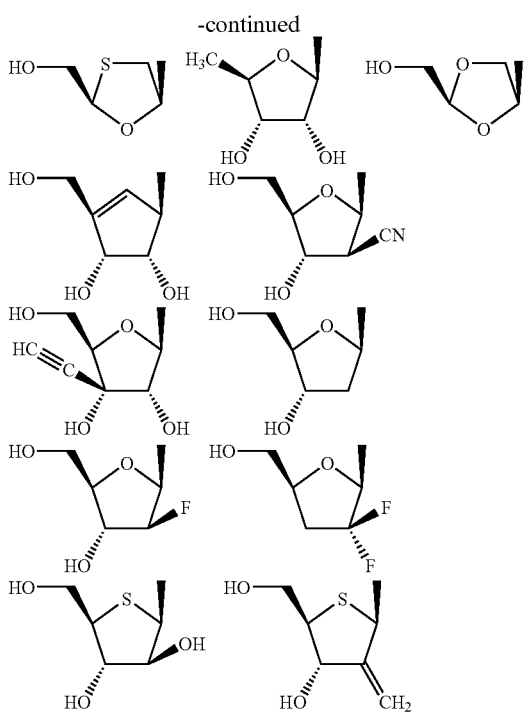

(7) The high molecular weight derivative of a nucleic acid antimetabolite according to (6) above, wherein R is a methyl group; A is an acetyl group, m is from 10 to 60 as an average value, n is from 100 to 300 as an average value, and the nucleic acid antimetabolite residue is a residue of gemcitabine or doxifluridine.

(8) The high molecular weight derivative of a nucleic acid antimetabolite according to any one of (3) to (7) above, wherein the hydrophobic substituent is an α-amino acid derivative represented by formula (4):

(4)

wherein Q represents the side chain of a neutral amino acid; and W represents a C1-C6 alkyl group or a benzyl group.

(9) The high molecular weight derivative of a nucleic acid antimetabolite according to (8) above, wherein Q is an isopropyl group or a benzyl group, and W is a benzyl group.

(10) The high molecular weight derivative of a nucleic acid antimetabolite according to any one of (3) to (7) above, wherein the hydrophobic substituent is a group represented by formula (5):

O-T (5)

wherein T represents a C1-C6 alkyl group which may be substituted with a phenyl group.

(11) The high molecular weight derivative of a nucleic acid antimetabolite according to (10) above, wherein T is a benzyl group, a 3-phenylpropyl group, a 4-phenylbutyl group or a 5-phenylpentyl group.

(12) The high molecular weight derivative of a nucleic acid antimetabolite according to (3) above, wherein R is a methyl group; A is an acetyl group; m is from 10 to 60 as an average value; n is from 100 to 300 as an average value; the nucleic acid antimetabolite residue is a gemcitabine residue; the hydrophobic substituent is a 4-phenylbutoxy group or a (1-benzyloxycarbonyl-2-phenyl)ethylamino group; and —N(R1)CONH(R2) is an isopropylaminocarbonylisopropylamino group.

(13) A high molecular weight derivative of a nucleic acid antimetabolite, obtained by linking a carboxyl group in the side chain of a high molecular weight compound comprising a polyethylene glycol moiety and a polymer moiety having a carboxyl group in the side chain, with a nucleic acid antimetabolite via an ester linkage, using a carbodiimide-based condensing agent in an organic solvent.

(14) An antitumor agent comprising the high molecular weight derivative of a nucleic acid antimetabolite according to any one of (1) to (13) above as an active ingredient.

(15) An antiviral agent comprising the high molecular weight derivative of a nucleic acid antimetabolite according to any one of (1) to (13) above as an active ingredient.

(16) A method for manufacturing the high molecular weight derivative of a nucleic acid antimetabolite according to any one of (1) to (12) above, comprising linking a carboxyl group in the side chain of the high molecular weight compound comprising a polyethylene glycol moiety and a polymer moiety having a carboxyl group in the side chain, with a nucleoside derivative of the nucleic acid antimetabolite via an ester linkage, using a carbodiimide-based condensing agent in an organic solvent.

EFFECTS OF THE INVENTION

The high molecular weight derivative of a nucleic acid antimetabolite of the present invention is characterized by having a structure in which a carboxyl group in the side chain of the high molecular weight compound comprising a polyethylene glycol moiety and a polymer moiety having a carboxyl group in the side chain is linked to a hydroxyl group of the nucleic acid antimetabolite via an ester linkage and to a certain hydrophobic residue. The high molecular weight derivative can remain in the blood in vivo for a long time and can slowly release the nucleic acid antimetabolite over a long time. Therefore, it is useful as an anticancer agent or antiviral agent having excellent therapeutic effect at lower doses. The high molecular weight derivative of a nucleic acid antimetabolite of the present invention is thought, in view of its structure, to form an aggregate having an outer shell formed of the polyethylene glycol moiety having high affinity with water and an inner shell formed of side chains having a hydrophobic residue or the nucleic acid antimetabolite, in water. Accordingly, the high molecular weight derivative has a property of slowly releasing drugs without depending on enzymes in vivo, and therefore can become a derivative of which the therapeutic effect is less affected by the individual differences in patients. Furthermore, the high molecular weight derivative of the present invention becomes a drug which selectively accumulates at the diseased sites and has superior effects while having lower adverse effects.

BEST MODE FOR CARRYING OUT THE INVENTION

The high molecular weight derivative of a nucleic acid antimetabolite of the present invention is characterized in that it is obtained by condensing, by dehydration, a carboxyl group in the side chain of a high molecular weight compound comprising a polyethylene glycol moiety and a polymer moiety having a carboxyl group in the side chain, with a hydroxyl group of a nucleic acid antimetabolite, using a carbodiimide-based condensing agent in an organic solvent.

The "nucleic acid antimetabolite" according to the present invention is a compound having antitumor activity or antiviral activity, and having the structure of a nucleoside derivative. More specifically, the "nucleic acid antimetabolite" is a compound in which the nucleic acid base moiety is any one selected from the aforementioned formula (2), and the group bound thereto (Rf) is any one selected from the aforementioned formula (3).

Even more specifically, examples of the nucleic acid antimetabolite of the present invention include, but not limited to, for example, cytarabine, gemcitabine, doxifluridine, azacitidine, decitabine, nelarabine, 2'-methylidene-2'-deoxycytidine (DMDC), tezacitabine, zalcitabine, lamivudine, 5'-deoxy-5-fluorocytidine (5'-DFCR), troxacitabine, 3'-ethynylcytidine, 2'-cyano-2'-deoxy-1-β-D-arabinofuranocylcytosine (CNDAC) or the like.

(6)

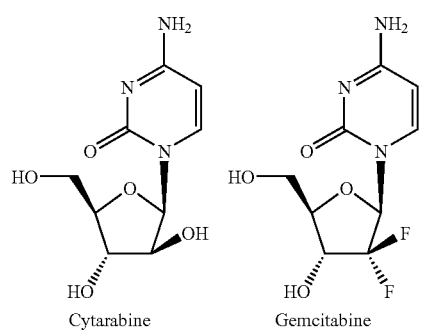

Cytarabine     Gemcitabine

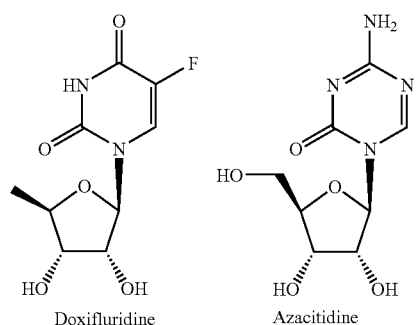

Doxifluridine     Azacitidine

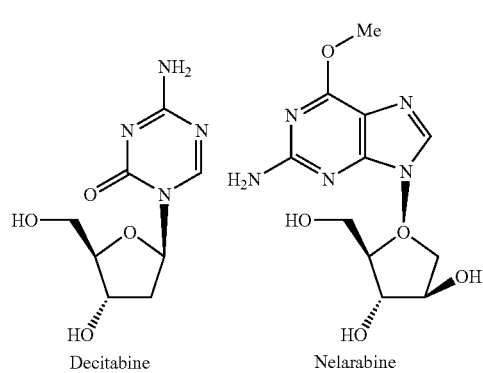

Decitabine     Nelarabine

-continued

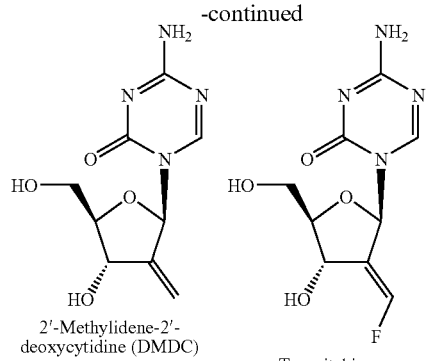

2'-Methylidene-2'-deoxycytidine (DMDC)     Tezacitabine

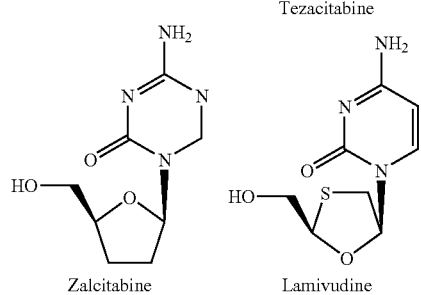

Zalcitabine     Lamivudine

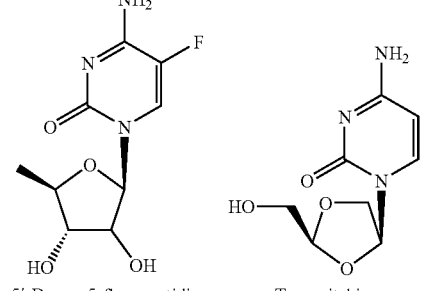

5'-Deoxy-5-fluorocytidine (5'-DFCR)     Troxacitabine

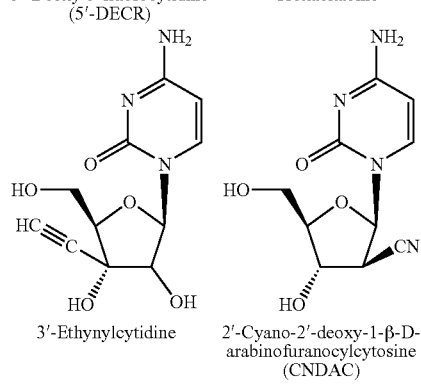

3'-Ethynylcytidine     2'-Cyano-2'-deoxy-1-β-D-arabinofuranocylcytosine (CNDAC)

As for the polymer moiety having a carboxyl group in the side chain in the "high molecular weight compound comprising a polyethylene glycol moiety and a polymer moiety having a carboxyl group in the side chain" according to the present invention, there may be mentioned a graft type polymer in which the side chain having a carboxyl group is branched out from the polymer backbone, a block type polymer resulting from condensation of a polycarboxylic acid polymer, or the like.

As for the aforementioned high molecular weight compound in which the polymer moiety having a carboxyl group in the side chain is a graft type polymer, there may be mentioned, for example, the polymer described in JP-A No. 11-279083, which is obtained by subjecting polyethylene glycol, a condensate of an acrylic acid, and an acrylic acid or maleic anhydride to a copolymerization reaction, and if necessary, subjecting the product to a hydrolysis reaction, or the like.

As for the aforementioned high molecular weight compound in which the polymer moiety having a carboxyl group in the side chain is a block type polymer, there may be mentioned a compound in which a polyethylene glycol having terminal functional groups is linked to a polycarboxylic acid having terminal functional groups, or the compound described in Patent Document 3, which is obtain able by a polymerization reaction in which activated amino acids capable of initiating polymerization are linked to a polyethylene glycol having amino groups at the ends of the chain.

Examples of the polymer having a carboxyl group in the side chain include polyacrylic acid, polymethacrylic acid, polymalic acid, polyglutamic acid, and the like, and polyglutamic acid is preferred.

The "polyethylene glycol" according to the present invention may also be a polyethylene glycol derivative modified at both ends of chain or at a single end of chain, and in that case, the modifying groups at the both ends of the chain may be identical or different. As the modifying group at the end of the chain, a C1-C6 alkyl group which may be substituted may be mentioned, and a C1-C4 alkyl group which may be substituted is preferred.

As for the C1-C6 alkyl group in the C1-C6 alkyl group which may be substituted, there may be mentioned a straight-chained, branched or cyclic C1-C6 alkyl group, and examples thereof include a methyl group, an ethyl group, a propyl group, an isopropyl group, a butyl group, an isobutyl group, a tert-butyl group, a pentyl group, an isopentyl group, a 2-methylbutyl group, a neopentyl group, a 1-ethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a cyclopropyl group, a cyclopentyl group, a cyclohexyl group, and the like. A C1-C4 alkyl group is preferred, and examples thereof include a methyl group, an ethyl group, an n-propyl group, an isopropyl group, an n-butyl group, an s-butyl group, a t-butyl group, and the like. Particularly preferred is a methyl group, an ethyl group, an n-propyl group or an isopropyl group.

The substituent for the C1-C6 alkyl group which may be substituted is not particularly limited. For example, an amino group, a methylamino group, a dimethylamino group, an ethylamino group, a diethylamino group, and the like may be mentioned, and an amino group is preferred.

According to the present invention, a polyethylene glycol derivative modified at both ends is preferred, and specifically, a polyethylene glycol derivative having a C1-C6 alkyl group at one end and an amino-C1-C6 alkyl group at the other end may be mentioned. A polyethylene glycol derivative having a C1-C4 alkyl group at one end and an amino-C1-C4 alkyl group at the other end is preferred, and particularly, a polyethylene glycol derivative having a methyl group at one end and an aminopropyl group at the other end is preferred.

The weight average molecular weight of the "polyethylene glycol" according to the present invention is about 200 to 500,000, preferably about 500 to 100,000, and more preferably about 2,000 to 50,000.

The "high molecular weight compound comprising a polyethylene glycol moiety and a polymer moiety having a carboxyl group in the side chain" according to the present invention is preferably a block type polymer, and more preferably a block copolymer of a polyethylene glycol and a polymer having a carboxyl group in the side chain.

The block copolymer of a polyethylene glycol and a polymer having a carboxyl group in the side chain may be exemplified by alkoxypolyethylene glycol-polyacrylic acid, alkoxypolyethylene glycol-polymethacrylic acid, alkoxypolyethylene glycol-polyglutamic acid, or the like, and methoxypolyethylene glycol-polyglutamic acid is preferred.

The average number of carboxyl group per molecule of the "high molecular weight compound comprising a polyethylene glycol moiety and a polymer moiety having a carboxyl group in the side chain" according to the present invention is about 3 to 200, preferably about 5 to 100, and more preferably about 10 to 60.

The weight average molecular weight of the "high molecular weight compound comprising a polyethylene glycol moiety and a polymer moiety having a carboxyl group in the side chain" according to the present invention is about 500 to 500,000, preferably about 2,000 to 100,000, and more preferably about 3,000 to 50,000.

According to the present invention, the amount of the nucleic acid antimetabolite linked via an ester linkage to the high molecular weight compound comprising a polyethylene glycol moiety and a polymer moiety having a carboxyl group in the side chain, is not particularly limited as long as the amount is in the range of 1 to the total number of the carboxyl groups, and is favorably an amount exhibiting efficacy when administered in vivo. Preferably, the amount is 5 to 100%, and more preferably 5 to 70%, of the total number of the carboxyl groups in the polymer moiety.

The aforementioned linking amount can be determined from the intensity of the ultra violet absorption spectrum of the compound of the present invention. Furthermore, the amount of binding can also be determined by quantifying the nucleic acid antimetabolite which is released by alkali-hydrolyzing the high molecular weight derivative of a nucleic acid antimetabolite of the present invention, for example, by high performance liquid chromatography or the like.

As a representative compound of the high molecular weight derivative of a nucleic acid antimetabolite of the present invention, there may be mentioned a compound represented by the aforementioned formula (1), wherein R represents a hydrogen atom or a C1-C6 alkyl group; A represents a hydrogen atom, a C1-C6 acyl group or a C1-C6 alkoxycarbonyl group; m represents from 3 to 200 as an average value; n represents from 5 to 2000 as an average value; X represents a group essentially including a nucleic acid antimetabolite residue and —N(R1)CONH(R2), the group being selected from the group consisting of a nucleic acid antimetabolite residue, a hydroxyl group, a hydrophobic substituent, and —N(R1)CONH(R2), wherein R1 and R2 may be identical or different, and are each a C1-C6 alkyl group which may be substituted with a tertiary amino group, (that is, two or more groups selected from the group consisting of a nucleic acid antimetabolite residue, a hydroxyl group, a hydrophobic substituent, and —N(R1)CONH(R2), in which the nucleic acid antimetabolite residue and —N(R1)CONH(R2) are essential, while the others are optional); and preferably, among m units, 5 to 95% have a nucleic acid antimetabolite residue for X, 0 to 95% have a hydroxyl group for X, 0 and 80% have a hydrophobic substituent for X, and 5 to 80% have —N(R1)CONH(R2) for X].

In the formula (1), the C1-C6 alkyl group for R has the same meaning as the above-described alkyl group, and preferred groups are also the same.

In the formula (1), the C1-C6 acyl group for A may be exemplified by a formyl group, an acetyl group, a propionyl group, a butyryl group, an isobutyryl group, a valeryl group, an isovaleryl group, a pivaloyl group or a hexanoyl group, and preferred is a C2-C4 acyl group, for example, an acetyl group or a propionyl group, and an acetyl group is more preferred.

In the formula (1), the C1-C6 alkoxycarbonyl group for A may be exemplified by a methoxycarbonyl group, an ethoxycarbonyl group, a propoxycarbonyl group, an isopropoxycarbonyl group, an n-butoxycarbonyl group, a tert-butoxycarbonyl group, a pentoxycarbonyl group, a hexyloxycarbonyl group, a cyclopropoxycarbonyl group, a cyclopentyloxycarbonyl group or a cyclohexyloxycarbonyl group, and preferred are a methoxycarbonyl group, an ethoxycarbonyl group, a propoxycarbonyl group, an isopropoxycarbonyl group, a butoxycarbonyl group and a tert-butoxycarbonyl group, and an ethoxycarbonyl group or a tert-butoxycarbonyl group is more preferred.

In the formula (1), m is from 3 to 200 as an average value, preferably about from 5 to 100, and more preferably about from 10 to 60.

In the formula (1), n is from 5 to 2000 as an average value, preferably about from 50 to 1000, and more preferably about from 100 to 300.

In the formula (1) of the high molecular weight derivative of a nucleic acid antimetabolite of the present invention, a glutamic acid derivative having a nucleic acid antimetabolite residue for X, a glutamic acid derivative having a hydroxyl group for the X, a glutamic acid derivative having a hydrophobic substituent for the X, and a glutamic acid derivative having —N(R1)CONH(R2) for the X, may be randomly linked, or may be linked such that the glutamic acid derivatives with different types of X respectively form blocks. Particularly preferred nucleic acid antimetabolite for X in the formula (1) is gemcitabine.

The hydrophobic substituent for X in the formula (1) includes various substituents, and the substituent is not particularly limited as long as it does not affect the manifestation of efficacy of the high molecular weight derivative of a nucleic acid antimetabolite. Preferably, there may be mentioned an α-amino acid derivative represented by the aforementioned formula (4), wherein Q represents the side chain of a neutral amino acid, and W represents a C1-C6 alkyl group or a benzyl group, or a group represented by the aforementioned formula (5), wherein T represents a C1-C6 alkyl group which may be substituted with a phenyl group.

The side chain of a neutral amino acid for Q in the formula (4) includes, for example, side chains for natural amino acid residues, such as a hydrogen atom, a methyl group, an isopropyl group, an isobutyl group, an s-butyl group, a benzyl group, a hydroxymethyl group, a 1-hydroxyethyl group, a carbamoylmethyl group and a 2-carbamoylethyl group; side chains for amino acid residue derivatives, such as a tert-butoxymethyl group, a benzyloxymethyl group, a benzyloxycarbonylmethyl group and a 2-benzyloxycarbonylethyl group; and the like. An isopropyl group, an isobutyl group, an s-butyl group, a benzyl group, a benzyloxymethyl group, a benzyloxycarbonylmethyl group, a 2-benzyloxycarbonylethyl group and the like are preferred, and an isopropyl group, a benzyl group, a benzyloxymethyl group or a 2-benzyloxycarbonylethyl group is more preferred, and an isopropyl group or a benzyl group is particularly preferred.

The C1-C6 alkyl group for W in the formula (4) may be exemplified by the same groups as the alkyl groups mentioned above, and preferred groups are also the same.

The C1-C6 alkyl group for T in the formula (5) has the same meaning as the alkyl group mentioned above, and preferred groups are also the same. Examples of the group represented by the formula (5) include a methoxy group, an ethoxy group, an n-propoxy group, an isopropoxy group, an n-butoxy group, a tert-butoxy group, an n-pentyloxy group, an n-hexyloxy group, a cyclopropyloxy group, a cyclopentyloxy group, a cyclohexyloxy group, a cyclohexylmethoxy group, a benzyloxy group, a 2-phenethyloxy group, a 3-phenylpropoxy group, a 4-phenylbutoxy group, a 5-phenylpentyloxy group, a diphenylmethoxy group, and the like.

The aforementioned hydrophobic substituent may also be exemplified by, for example, an amino group such as a methylamino group, an ethylamino group, an n-propylamino group, an isopropylamino group, an n-butylamino group, an isobutylamino group, an n-pentylamino group, an n-hexylamino group, a cyclopropylamino group, a cyclopentylamino group, a cyclohexylamino group, a cyclohexylmethylamino group, a dicyclohexylmethylamino group, an anilino group, a benzylamino group, a 2-phenethylamino group, a 3-phenylpropylamino group, a 4-phenylbutylamino group or a diphenylmethylamino group.

As the hydrophobic substituent for X in the formula (1), a benzyloxy group, a 3-phenylpropoxy group, a 4-phenylbutoxy group, a (1-benzyloxycarbonyl-2-methyl)propylamino group, or a (1-benzyloxycarbonyl-2-phenyl)ethylamino group is particularly preferred, and a 4-phenylbutoxy group or a (1-benzyloxycarbonyl-2-phenyl)ethylamino group is especially preferred.

The group —N(R1)CONH(R2) for X in the formula (1) is not particularly limited as long as it does not affect the manifestation of efficacy of the high molecular weight derivative of a nucleic acid antimetabolite. Preferably, R1 and R2 of the —N(R1)CONH(R2) may be identical or different, and are each a group represented by a C1-C6 alkyl group which may be substituted with a tertiary amino group. More preferably, the group is a cyclohexylaminocarbonylcyclohexylamino group, or an isopropylaminocarbonylisopropylamino group.

In addition, the C1-C6 alkyl group of the C1-C6 alkyl group which may be substituted with a tertiary amino group for R1 and R2 of the —N(R1)CONH(R2), has the same meaning as the alkyl group mentioned above, and preferred groups are also the same.

In the formula (1), the proportion of X being a nucleic acid antimetabolite residue, with respect to the total number of carboxyl groups of the polymer moiety (a number equal to m), is 5 to 95%, and preferably 5 to 70%; the proportion of X being a hydroxyl group is 0 to 95%, and preferably 5 to 70%; the proportion of X being a hydrophobic substituent is 0 to 80%, and preferably 20 to 70%; and the proportion of X being —N(R1)CONH(R2) is 5 to 80%, and preferably 5 to 70%.

In the high molecular weight derivative of a nucleic acid antimetabolite of the present invention, when there are side chain carboxyl groups not bound by a nucleic acid antimetabolite or the like, these carboxyl groups may be in a free form, or in the form of a salt of an alkali. In the case where the carboxyl group has been obtained in a free form, the carboxyl group can be converted to a desired salt according to a known method or a method equivalent thereto. On the other hand, in the case where the carboxyl group has been obtained as a salt, the salt can be converted to a free form or another desired salt according to a known method or a method equivalent thereto.

Examples of the salt of an alkali include lithium salts, sodium salts, potassium salts, magnesium salts, ammonium salts, triethylammonium salts, and the like.

The structural unit constituting the polymer moiety having a carboxyl group in the side chain in the high molecular weight derivative of a nucleic acid antimetabolite of the present invention, may be an optically active form in the case where optical isomers exist, or a racemic form, or a mixture at an arbitrary ratio. For example, if the polymer moiety having a carboxyl group in the side chain is a polyglutamic acid derivative, a polymer in which poly-L-glutamic acid, poly-D-glutamic acid, L-glutamic acid having a substituted side chain, and D-glutamic acid having a substituted side chain are linked at any proportions in any order of linkage, is acceptable.

As a compound that is particularly preferred as the high molecular weight derivative of a nucleic acid antimetabolite of the present invention, for example, the compounds indicated in the following Table 1 may be mentioned.

In the Table 1, the "proportion" shown under each X means the proportion (%) of each of the substituents for X being bound with respect to the total number of carboxyl groups of the polymer moiety (which equals to m), and represents an approximate value. The remainder other than the substituents shown in the table is a hydroxyl group. Bzl represents a benzyl group, Phe represents phenylalanine, and C4H8Ph represents a 4-phenylbutyl group. The nucleic acid antimetabolite residue for X may include the respective residues of cytarabine, gemcitabine, doxifluridine, azacitidine, decitabine, nelarabine, tezacitabine, 5'-deoxy-5-fluorocytidine, 2'-deoxy-2'-methylidenecytidine (DMDC), 3'-ethynylcytidine, 2'-C-cyano-2'-deoxy-1-beta-D-arabinofuranocylcytosine (CNDAC), troxacitabine, and (−)-beta-L-dioxolanecytidine.

TABLE 1

| Compound No. | R | n (average) | m (average) | A | X: Nucleic acid antimetabolite (proportion) | X: Hydrophobic substituent (proportion) | X: —N(R1)CONH(R2) (proportion) |
|---|---|---|---|---|---|---|---|
| 1 | CH$_3$ | 272 | 26 | CH$_3$CO | Gemcitabine (25%) | Phe-OBzl (45%) | Isopropylaminocarbonylisopropylamino group (15%) |
| 2 | CH$_3$ | 272 | 26 | CH$_3$CO | Gemcitabine (10%) | Phe-OBzl (70%) | Isopropylaminocarbonylisopropylamino group (5%) |
| 3 | CH$_3$ | 272 | 26 | CH$_3$CO | Gemcitabine (20%) | OC4H8Ph (40%) | Isopropylaminocarbonylisopropylamino group (15%) |
| 4 | CH$_3$ | 272 | 26 | CH$_3$CO | Gemcitabine (15%) | OC4H8Ph (60%) | Isopropylaminocarbonylisopropylamino group (10%) |
| 5 | CH$_3$ | 272 | 26 | CH$_3$CO | Doxifluridine (30%) | Phe-OBzl (30%) | Isopropylaminocarbonylisopropylamino group (20%) |
| 6 | CH$_3$ | 272 | 26 | CH$_3$CO | Gemcitabine (20%) | Phe-OBzl (55%) | Isopropylaminocarbonylisopropylamino group (10%) |
| 7 | CH$_3$ | 272 | 26 | CH$_3$CO | Gemcitabine (15%) | Phe-OBzl (60%) | Isopropylaminocarbonylisopropylamino group (10%) |
| 8 | CH$_3$ | 272 | 26 | CH$_3$CO | Gemcitabine (20%) | OC4H8Ph (50%) | Isopropylaminocarbonylisopropylamino group (15%) |
| 9 | CH$_3$ | 272 | 26 | CH$_3$CO | Cytarabine (25%) | Phe-OBzl (45%) | Isopropylaminocarbonylisopropylamino group (15%) |
| 10 | CH$_3$ | 272 | 26 | CH$_3$CO | Doxifluridine (25%) | Phe-OBzl (45%) | Isopropylaminocarbonylisopropylamino group (15%) |
| 11 | CH$_3$ | 272 | 26 | CH$_3$CO | Azacitidine (25%) | Phe-OBzl (45%) | Isopropylaminocarbonylisopropylamino group (15%) |
| 12 | CH$_3$ | 272 | 26 | CH$_3$CO | Decitabine (25%) | Phe-OBzl (45%) | Isopropylaminocarbonylisopropylamino group (15%) |
| 13 | CH$_3$ | 272 | 26 | CH$_3$CO | Nelarabine (25%) | Phe-OBzl (45%) | Isopropylaminocarbonylisopropylamino group (15%) |
| 14 | CH$_3$ | 272 | 26 | CH$_3$CO | Tezacitabine (25%) | Phe-OBzl (45%) | Isopropylaminocarbonylisopropylamino group (15%) |
| 15 | CH$_3$ | 272 | 26 | CH$_3$CO | 5'-Deoxy-5-fluorocytidine (25%) | Phe-OBzl (45%) | Isopropylaminocarbonylisopropylamino group (15%) |
| 16 | CH$_3$ | 272 | 26 | CH$_3$CO | 3'-Ethynylcytidine (25%) | Phe-OBzl (45%) | Isopropylaminocarbonylisopropylamino group (15%) |
| 17 | CH$_3$ | 272 | 26 | CH$_3$CO | 2'-C-cyano-2'-deoxy-1-beta-D-arabinofuranocylcytosine (25%) | Phe-OBzl (45%) | Isopropylaminocarbonylisopropylamino group (15%) |
| 18 | CH$_3$ | 272 | 26 | CH$_3$CO | Troxacitabine (25%) | Phe-OBzl (45%) | Isopropylaminocarbonylisopropylamino group (15%) |
| 19 | CH$_3$ | 272 | 26 | CH$_3$CO | (−)-beta-L-dioxolanecytidine (25%) | Phe-OBzl (45%) | Isopropylaminocarbonylisopropylamino group (15%) |
| 20 | CH$_3$ | 272 | 26 | CH$_3$CO | Cytarabine (15%) | Phe-OBzl (60%) | Isopropylaminocarbonylisopropylamino group |

TABLE 1-continued

| Compound No. | R | n (average) | m (average) | A | X: Nucleic acid antimetabolite (proportion) | X: Hydrophobic substituent (proportion) | X: —N(R1)CONH(R2) (proportion) |
|---|---|---|---|---|---|---|---|
| 21 | $CH_3$ | 272 | 26 | $CH_3CO$ | Doxifluridine (15%) | Phe-OBzl (60%) | Isopropylaminocarbonylisopropylamino group (10%) |
| 22 | $CH_3$ | 272 | 26 | $CH_3CO$ | Azacitidine (15%) | Phe-OBzl (60%) | Isopropylaminocarbonylisopropylamino group (10%) |
| 23 | $CH_3$ | 272 | 26 | $CH_3CO$ | Decitabine (15%) | Phe-OBzl (60%) | Isopropylaminocarbonylisopropylamino group (10%) |
| 24 | $CH_3$ | 272 | 26 | $CH_3CO$ | Nelarabine (15%) | Phe-OBzl (60%) | Isopropylaminocarbonylisopropylamino group (10%) |
| 25 | $CH_3$ | 272 | 26 | $CH_3CO$ | Tezacitabine (15%) | Phe-OBzl (60%) | Isopropylaminocarbonylisopropylamino group (10%) |
| 26 | $CH_3$ | 272 | 26 | $CH_3CO$ | 5'-Deoxy-5-fluorocytidine (15%) | Phe-OBzl (60%) | Isopropylaminocarbonylisopropylamino group (10%) |
| 27 | $CH_3$ | 272 | 26 | $CH_3CO$ | 3'-Ethynylcytidine (15%) | Phe-OBzl (60%) | Isopropylaminocarbonylisopropylamino group (10%) |
| 28 | $CH_3$ | 272 | 26 | $CH_3CO$ | 2'-C-cyano-2'-deoxy-1-beta-D-arabinofuranocylcytosine (15%) | Phe-OBzl (60%) | Isopropylaminocarbonylisopropylamino group (10%) |
| 29 | $CH_3$ | 272 | 26 | $CH_3CO$ | Troxacitabine (15%) | Phe-OBzl (60%) | Isopropylaminocarbonylisopropylamino group (10%) |
| 30 | $CH_3$ | 272 | 26 | $CH_3CO$ | (−)-beta-L-dioxolanecytidine (15%) | Phe-OBzl (60%) | Isopropylaminocarbonylisopropylamino group (10%) |

The high molecular weight derivative of a nucleic acid antimetabolite of the present invention can be produced by, for example, condensing a methoxypolyethylene glycol-polyglutamic acid block copolymer produced according to the method described in Patent Document 3, with a nucleic acid antimetabolite, in a solvent using a dehydrating condensing agent, but the production method is not limited to this particular method.

The solvent for the aforementioned reaction is not particularly limited as long as the reaction can proceed. The examples of the solvent include, for example, aromatic hydrocarbons such as toluene and xylene; halogenated hydrocarbons such as methylene chloride, chloroform and 1,2-dichloroethane; ethers such as tetra hydrofuran, dioxane, dimethoxyethane, and diethylene glycol dimethyl ether; nitriles such as acetonitrile and propionitrile; amides such as dimethylformamide, dimethylacetamide, and N-methylpyrrolidone; ureas such as 1,3-dimethylimidazolidinone; or solvent mixtures of the above-mentioned solvents, and the like. Amides and ureas are preferred, and dimethylformamide or 1,3-dimethylimidazolidinone is more preferred.

The dehydrating condensing agent for the above-described reaction is not particularly limited as long as the condensation reaction between a hydroxyl group of a nucleotide derivative which is a nucleic acid antimetabolite and a carboxyl group proceeds. Preferably, carbodiimide-based condensing agents such as dicyclohexylcarbodiimide, diisopropylcarbodiimide, and 1-dimethylaminopropyl-3-ethylcarbodiimide may be mentioned.

During the dehydration condensation reaction, a reaction aid may also be used, and examples of the reaction aid include N-hydroxysuccinimide, 1-hydroxybenzotriazole or 4-dimethylaminopyridine, 2,6-di-t-butyl-4-methylpyridine, and the like.

The reaction temperature of the dehydration condensation reaction is usually 4 to 60° C., and preferably 15 to 50° C. The reaction time is from 2 hours to several days, and preferably 4 to 48 hours.

After the reaction, the target compound can be isolated and purified, if necessary, by appropriately applying separation techniques that are known per se, for example, concentration under reduced pressure, solvent extraction, crystallization, dialysis, chromatography and the like.

The above-described dehydration condensation reaction gives a high molecular weight derivative in which X is the groups selected from the group consisting of a nucleic acid antimetabolite residue, a hydroxyl group, —N(R1)CONH(R2), wherein R1 and R2 may be identical or different, and are each a C1-C6 alkyl group which may be substituted with a tertiary amino group. Furthermore, the mode of linkage between the polymer carrier of the high molecular weight derivative obtained by this dehydration condensation reaction and the nucleic acid antimetabolite, will be mostly ester linkage, since a carbodiimide-based condensing agent is used. There may be cases where a linkage form other than the ester linkage may be obtained depending on the nucleic acid antimetabolite, but as long as the mode of linkage does not affect the manifestation of efficacy of the high molecular weight derivative of a nucleic acid antimetabolite, the other mode of linkage may be mixed, or the ester linkage may be exclusive.

In the case where only —N(R1)CONH(R2) (wherein R1 and R2 may be identical or different, and are each a C1-C6 alkyl group which may be substituted with a tertiary amino group) is introduced to the high molecular weight compound carrier as X, the dehydration condensation reaction between the nucleic acid antimetabolite and the high molecular weight compound can be carried out in the absence of the nucleic acid antimetabolite.

When the high molecular weight derivative of a nucleic acid antimetabolite of the present invention has a hydrophobic substituent, this high molecular weight derivative can be produced by condensing unsubstituted carboxyl groups in the side chain of a high molecular weight compound comprising a polyethylene glycol moiety which is obtained by introducing a hydrophobic substituent to a portion of the carboxyl groups of a methoxypolyethylene glycol-polyglutamic acid block copolymer produced according to the method described in Patent Document 3, and a polymer moiety having a carboxyl group in the side chain, with a nucleoside derivative which is a nucleic acid antimetabolite, in an organic solvent using a dehydrating condensing agent in the same manner as described above.

Introduction of a hydrophobic substituent can be achieved, for example, in the case where the hydrophobic substituent is an alkoxy group, by condensing (esterifying) a corresponding alcohol and the carboxyl group in a solvent using a dehydrating condensing agent, or by subjecting a corresponding halogenated alkyl or the like and the carboxyl group to a nucleophilic substitution reaction in a solvent in the presence of a base, and for example, in the case where the hydrophobic substituent is a substituted amino group, by condensing (amidating) a corresponding amine and the carboxyl group in a solvent using a dehydrating condensing agent.

The solvent for the above-described dehydration condensation reaction (esterification reaction) is not particularly limited as long as the reaction proceeds, but a solvent such as the solvent which can be used in the dehydration condensation of the above-mentioned methoxypolyethylene glycol-polyglutamic acid block copolymer and a nucleic acid antimetabolite, can be used, and preferred solvents are also similar. The dehydrating condensing agent is not particularly limited as long as the dehydration condensation reaction between an alcohol and a carboxyl group proceeds, but the dehydrating condensing agent is preferably dicyclohexylcarbodiimide, diisopropylcarbodiimide, 1-dimethylaminopropyl-3-ethylcarbodiimide, carbonyldiimidazole, isobutyl chloroformate or pivalic acid chloride.

During the dehydration condensation reaction, a reaction aid may also be used, and examples of the reaction aid include N-hydroxysuccinimide, 1-hydroxybenzotriazole or 4-dimethylaminopyridine, 2,6-di-t-butyl-4-methylpyridine and the like.

The reaction temperature of the dehydration condensation reaction is usually 4 to 60° C., and preferably 15 to 50° C. The reaction time is from 2 hours to several days, and preferably 4 to 48 hours.

The solvent for the above-described nucleophilic substitution reaction is not particularly limited as long as the reaction proceeds, but a solvent such as the solvent which can be used in the dehydration condensation of the above-mentioned methoxypolyethylene glycol-polyglutamic acid block copolymer and a nucleic acid antimetabolite, can be used, and preferred solvents are also similar. Examples of the base include alkali metal carbonates such as lithium carbonate, sodium carbonate and potassium carbonate; alkali metal hydrides such as lithium hydride, sodium hydride and potassium hydride; alkali metal hydroxides such as lithium hydroxide, sodium hydroxide and potassium hydroxide; alkali metal alkoxides such as lithium methoxide, sodium methoxide, sodium ethoxide, and potassium tert-butoxide; organic amines such as triethylamine, tributylamine, N,N-diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO), and 1,8-diazabicyclo[5.4.0]-7-undecene (DBU); and the like. Preferred bases are alkali metal carbonates, alkali metal hydrides or organic amines.

The reaction temperature of the nucleophilic substitution reaction is usually 4 to 60° C., and preferably room temperature to 50° C. The reaction time is from 1 hour to several days, and preferably 4 to 48 hours.

The solvent for the dehydration condensation reaction (amidation reaction) is not particularly limited as long as the reaction proceeds, but a solvent such as the solvent which can be used in the dehydration condensation of the above-mentioned methoxypolyethylene glycol-polyglutamic acid block copolymer and a nucleic acid antimetabolite, can be used, and preferred solvents are also similar. The dehydrating condensing agent is not particularly limited as long as the condensation reaction between an amine and a carboxyl group proceeds, but the dehydrating condensing agent is preferably dicyclohexylcarbodiimide, diisopropylcarbodiimide, 1-dimethylaminopropyl-3-ethylcarbodiimide, carbonyldiimidazole, isobutyl chloroformate, pivalic acid chloride, DMT-MM (4-(4,6-dimethoxy-1,3,5-triazin-2-yl)-4-methylmorpholinium chloride), TFFH (tetramethylfluoroformamidinium hexa fluorophosphate), 1-ethoxycarbonyl-2-ethoxy-1,2-dihydroxyquinolinone (EEDQ), or BOP (benzotriazol-1-yloxytris(dimethylamino) phosphonium hexa fluorophosphate).

During the dehydration condensation reaction, a reaction aid may also be used, and examples of the reaction aid include N-hydroxysuccinimide, 1-hydroxybenzotriazole or 4-dimethylaminopyridine, 2,6-di-t-butyl-4-methylpyridine, and the like.

The reaction temperature of the dehydration condensation reaction is usually 4 to 60° C., and preferably room temperature to 50° C. The reaction time is from 1 hour to several days, and preferably 4 to 48 hours.

In addition, since the order of binding of the groups selected from the group consisting of a hydrophobic substituent, a nucleic acid antimetabolite and —N(R1)CONH(R2), to the high molecular weight compound is not of significant importance, the reaction may be carried out with a mixture of those groups. However, in order to avoid the reaction and decomposition of the nucleic acid antimetabolite which is a main active component having a polyfunctional group, it is preferable to introduce a hydrophobic substituent to the high molecular weight compound, and then to link the nucleic acid antimetabolite and —N(R1)CONH(R2) thereto.

The high molecular weight derivative of a nucleic acid antimetabolite of the present invention may form, in an aqueous solution, a micelle having the polyethylene glycol moiety as an outer shell. The formation of micelles can be verified by a gel permeation chromatography (GPC) method, a dynamic light scattering method, or the like.

According to the present invention, when a carboxyl group not having a nucleic acid antimetabolite bound thereto is bound to a hydrophobic substituent, micelles can be formed more easily.

The present invention also includes an antitumor agent or antiviral agent, which comprises the high molecular weight derivative of a nucleic acid antimetabolite described above as an active ingredient. The high molecular weight derivative of a nucleic acid antimetabolite can be administered directly, or can also be administered as a pharmaceutical composition in which the high molecular weight derivative is mixed with pharmaceutically acceptable materials. The dosage form of the pharmaceutical composition may be anyone of injections, powders, granules, tablets, suppository, and the like. These preparations may also contain various auxiliary agents that are used for pharmaceutical purposes, namely, carriers or other aids, for example, additives such as stabilizers, preservatives, soothing agents and emulsifiers.

The content of the high molecular weight derivative of a nucleic acid antimetabolite in the preparation may vary with the preparation, but the content is usually 0.1 to 100% by weight, and preferably 1 to 98% by weight.

The application of the antitumor agent of the present invention, which comprises the high molecular weight derivative of a nucleic acid antimetabolite as an active ingredient, is not particularly limited, but the antitumor agent can be used for, for example, non-small cell lung cancer, pancreatic cancer, gastric cancer, colon cancer, rectal cancer, breast cancer, ovarian cancer, bladder cancer, AIDS-associated Kaposi's sarcoma, and the like.

The application of the antiviral agent of the present invention, which comprises the high molecular weight derivative of a nucleic acid antimetabolite as an active ingredient, is not particularly limited, but for example, the antiviral agent can be used for acquired immunodeficiency syndrome (AIDS), herpes zoster, herpes simplex virus infection, and the like, and can also be used for the purpose of preventing infection.

As for the method of administering the high molecular weight derivative of a nucleic acid antimetabolite of the present invention, any method of administration such as oral, injection, rectal administration, intraportal administration, mixing with the perfusate of an organ, or topical administration to the organ of diseased site, can be used. However, parenteral administration is preferred, and more preferred is intravenous administration by injection, intraarterial administration, or topical administration to the organ of diseased site. The dosage of the high molecular weight derivative of a nucleic acid antimetabolite of the present invention varies with the disease condition, method of administration, condition, age and weight of the patient, and the like, but the dosage is usually 1 mg to 5000 mg, and preferably 10 mg to 2000 mg, in terms of the nucleic acid antimetabolite, per $m^2$ of the body surface area, and this may be administered once a day or in several divided portions a day. Furthermore, while this administration can be carried out for several consecutive days, the administration can also be repeated at an interval of several days or several months. If necessary, methods of administration, dosage and administration schedule other than those described above can also be used.

The case where the high molecular weight derivative of the present invention acts as a prodrug, is also included in the present invention. Here, the prodrug is a chemical derivative of a biologically active parent compound, which liberates the parent compound in vivo when administered.

EXAMPLES

Hereinafter, the present invention will be described in more detail by presenting Examples, Reference Examples and Test Examples, but the scope of the present invention is not intended to be limited to these examples.

Reference Example 1

Synthesis of N-Acetylation Product of Block Copolymer of Monomethoxypolyethylene Glycol Having a Molecular Weight of about 12000 and Polyglutamic Acid Having a Polymerization Number of about 26

A polyethylene glycol having a methoxy group at one end and a 3-aminopropyl group at the other end (SUNBRIGHT MEPA-12T, manufactured by Nippon Fat & Oil Co., Ltd., average molecular weight 12000, 7.74 g) was dissolved in dimethylsulfoxide (160 mL), and γ-benzyl-L-glutamate N-carboxylic acid anhydride (BLG-NCA, 5.1 g; 30 equivalents relative to the polyethylene glycol) was added thereto. The mixture was stirred overnight at 30° C. The reaction liquid was added dropwise to a mixed solvent of isopropyl ether-ethanol (4:1, 2.4 L) under stirring, and the resulting mixture was stirred for another one hour. A precipitate separated out there from was collected by filtration, and was washed with a mixed solvent of isopropyl ether-ethanol (4:1, 400 mL). The obtained product (11.50 g) was dissolved in N,N-dimethylformamide (180 mL), acetic anhydride (3.45 mL) was added thereto, and the mixture was stirred overnight at 30° C. The mixture was added dropwise to a mixed solvent of isopropyl ether-ethyl acetate (4:1, 1.6 L) under stirring, and the resulting mixture was stirred for another one hour. A precipitate separated out there from was collected by filtration, and was washed with a mixed solvent of isopropyl ether-ethyl acetate (4:1, 400 mL). The obtained product (11.24 g) was dissolved in N,N-dimethylformamide (150 mL), 5% palladium-carbon (water content 55%, 1.00 g) was added thereto, and the mixture was stirred overnight at room temperature in a hydrogen atmosphere. The palladium-carbon was separated by filtration, and then the filtrate was added dropwise to a mixed solvent of isopropyl ether-ethyl acetate (4:1, 2.5 L) under stirring. The resulting mixture was stirred for another one hour. A precipitate separated out therefrom was collected by filtration, and was washed with a mixed solvent of isopropyl ether-ethyl acetate (4:1, 300 mL). The obtained product was dissolved in distilled water (500 mL), and the liquid was adjusted to pH 11 by adding a 1 M aqueous solution of sodium hydroxide. Distilled water was added to the solution to adjust the final liquid volume to 1000 mL, and sodium chloride (50 g) was added. This solution was passed through a column of adsorbent resin HP-20ss (manufactured by Mitsubishi Chemical Corp., 250 mL), washed with a 5% aqueous solution of sodium chloride (1000 mL) and distilled water (1000 mL), and eluted with a 50% aqueous solution of acetonitrile (1250 mL). The eluted fraction including the target product was eluted by passing through a column of a cation exchange resin Dowex 50W (proton type, 100 mL), and was further eluted with a 50% aqueous solution of acetonitrile (150 mL). The eluted fraction including the target product was concentrated under reduced pressure until the liquid volume reached about 150 mL, and then freeze-dried, to obtain the title compound (6.67 g).

The average polymerization number of glutamic acid (the number of carboxyl groups) per molecule of the subject compound, based on the titration value obtained by using an aqueous solution of sodium hydroxide, was 25.81.

Reference Example 2

Synthesis of N-Acetylation Product of Block Copolymer of Monomethoxypolyethylene Glycol Having a Molecular Weight of about 12000 and Polyglutamic Acid Having a Polymerization Number of about 26

The title compound was obtained according to the method described in Reference Example 1, by using 29.1 equivalents of BLG-NCA relative to the polyethylene glycol.

The average polymerization number of glutamic acid (the number of carboxyl groups) per molecule of the subject compound, based on the titration value obtained by using an aqueous solution of sodium hydroxide, was 26.72.

Reference Example 3

Synthesis of N-Acetylation Product of Block Copolymer of Monomethoxypolyethylene Glycol Having a Molecular Weight of about 12000 and Polyglutamic Acid Having a Polymerization Number of about 26

The title compound was obtained according to the method described in Reference Example 1, by using 30 equivalents of BLG-NCA relative to the polyethylene glycol.

The average polymerization number of glutamic acid (the number of carboxyl groups) per molecule of the subject compound, based on the titration value obtained by using an aqueous solution of sodium hydroxide, was 26.70.

Reference Example 4

Synthesis Of Amide Conjugate Of N-Acetylation Product of Block Copolymer of Monomethoxypolyethylene Glycol Having a Molecular Weight of about 12000 and Polyglutamic Acid Having a Polymerization Number of about 26, with L-Phenylalanine Benzyl Ester (about 45% with Respect to Carboxyl Groups of Polyglutamic Acid)

The N-acetylation product (596 mg) of a block copolymer of monomethoxypolyethylene glycol having a molecular weight about 12000 and polyglutamic acid having a polymerization number of about 26 as described in Reference Example 1, L-phenylalanine benzyl ester hydrochloride (128 mg), and N,N-diisopropylethylamine (77 μL) were dissolved in N,N-dimethylformamide (10 mL), DMT-MM (146 mg) was added there to, and the mixture was stirred overnight at 40° C. The reaction liquid was cooled to room temperature, and then was added dropwise to a mixed solvent of diisopropyl ether-ethanol (4:1, 100 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 2 mL) was added thereto, and the mixture was shaken at room temperature for 2 hours. The resin was removed by filtration, and the resin was washed with a 50% aqueous solution of acetonitrile. The resulting filtrate was concentrated under reduced pressure to a half the volume, and then was freeze-dried, to obtain the title compound (580 mg).

The subject compound was hydrolyzed, and then the benzyl alcohol liberated therefrom was quantified by high performance liquid chromatography (HPLC), to thereby determine the binding ratio of the Phe-OBzl group bound to the subject compound via an amide linkage. The binding ratio was 45.94% with respect to the carboxyl groups of the polyglutamic acid.

Method of Hydrolysis

The title compound (12.80 mg) was dissolved in methanol (1.0 mL), a 0.5 M aqueous solution of sodium hydroxide (1.0 mL) was added thereto, and the mixture was stirred for 1 hour at 40° C. The mixture was neutralized with acetic acid, and was diluted with distilled water, to obtain precisely 10 mL of the solution.

Analysis Conditions for HPLC (Analysis of Benzyl Alcohol)

Column: YMC Hydrosphere, 4.6φ×250 mm;
Column temperature: 40° C.;
Eluent liquid A: 1% aqueous solution of phosphoric acid, liquid B: acetonitrile;
Gradient: liquid B % (time, minutes) 0(0), 0(5), 80(25), 80(35), stop (35.01);
Flow rate: 1 mL/min;
Detector (detection wavelength): UV (210 nm)

Reference Example 5

Synthesis of Amide Conjugate of N-Acetylation Product of Block Copolymer of Monomethoxypolyethylene Glycol Having a Molecular Weight of about 12000 and Polyglutamic Acid Having a Polymerization Number of about 26, with L-Phenylalanine Benzyl Ester (about 70% with Respect to Carboxyl Groups of Polyglutamic Acid)

The N-acetylation product (596 mg) of a block copolymer of monomethoxypolyethylene glycol having a molecular weight about 12000 and polyglutamic acid having a polymerization number of about 26 as described in Reference Example 1, L-phenylalanine benzyl ester hydrochloride (193 mg), and N,N-diisopropylethylamine (115 μL) were dissolved in N,N-dimethylformamide (10 mL), DMT-MM (219 mg) was added there to, and the mixture was stirred overnight at 40° C. The reaction liquid was cooled to room temperature, and then was added dropwise to a mixed solvent of diisopropyl ether-ethanol (4:1, 100 mL) After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 2 mL) was added thereto, and the mixture was shaken at room temperature for 2 hours. The resin was removed by filtration, and the resin was washed with a 50% aqueous solution of acetonitrile. The resulting filtrate was concentrated under reduced pressure to a half the volume, and then was freeze-dried, to obtain the title compound (667 mg).

The subject compound was hydrolyzed by the same condition as in Reference Example 4, and then the benzyl alcohol liberated therefrom was quantified by high performance liquid chromatography (HPLC) under the same conditions as in Reference Example 4, to thereby determine the binding ratio of the Phe-OBzl group bound to the subject compound via an amide linkage. The binding ratio was 69.9% with respect to the carboxyl groups of the polyglutamic acid.

Reference Example 6

Synthesis of Ester Conjugate of N-Acetylation Product of Block Copolymer of Monomethoxypolyethylene Glycol Having a Molecular Weight of about 12000 and Polyglutamic Acid Having a Polymerization Number of about 26, with 4-Phenylbutyl Bromide (about 40% with Respect to Carboxyl Groups of Polyglutamic Acid)

The N-acetylation product (1.00 g) of a block copolymer of monomethoxypolyethylene glycol having a molecular weight about 12000 and polyglutamic acid having a polymerization number of about 26 as described in Reference Example 1, and 4-phenylbutyl bromide (161 mg) were dissolved in N,N-dimethylformamide (20 mL), 1,8-diazabicyclo[5.4.0]-7-undecene (DBU, 251 µL) was added thereto, and the mixture was stirred overnight at 40° C. The reaction liquid was cooled to room temperature, and then was added dropwise to a mixed solvent of diisopropyl ether-ethanol (4:1, 250 mL). After stirring the mixture for 30 minutes, a precipitate separated out there from was collected by filtration, and was washed with a mixed solvent of diisopropyl ether-ethanol (4:1). The obtained product was dissolved in a 60% aqueous solution of acetonitrile, a cation exchange resin Dowex 50W (proton type, 4 mL) was added thereto, and the mixture was shaken for 2 hours. The resin was removed by filtration, and the filtrate was freeze-dried, to obtain the title compound (1.027 g).

The subject compound was hydrolyzed by the same condition as in Reference Example 4, and then the 4-phenylbutanol liberated therefrom was quantified by high performance liquid chromatography (HPLC), to thereby determine the binding ratio of the 4-phenylbutoxy group bound to the subject compound. The binding ratio was 42.1% with respect to the carboxyl groups of the polyglutamic acid.

Reference Example 7

Synthesis of Ester Conjugate of N-Acetylation Product of Block Copolymer of Monomethoxypolyethylene Glycol Having a Molecular Weight of about 12000 and Polyglutamic Acid Having a Polymerization Number of about 26, with 4-Phenylbutyl Bromide (about 60% with Respect To Carboxyl Groups of Polyglutamic Acid)

The N-acetylation product (3.73 g) of a block copolymer of monomethoxypolyethylene glycol having a molecular weight about 12000 and polyglutamic acid having a polymerization number of about 26 as described in Reference Example 2, and 4-phenylbutyl bromide (1.05 g) were dissolved in N,N-dimethylformamide (91 mL), 1,8-diazabicyclo[5.4.0]-7-undecene (DBU, 897 L) was added thereto, and the mixture was stirred overnight at 40° C. The reaction liquid was cooled to room temperature, and then was added dropwise to a mixed solvent of diisopropyl ether-ethanol (4:1, 1.5 L). After stirring the mixture for 30 minutes, a precipitate separated out there from was collected by filtration, and was washed with a mixed solvent of diisopropyl ether-ethanol (4:1). The obtained product was dissolved in a 50% aqueous solution of acetonitrile, a cation exchange resin Dowex 50W (proton type, 15 mL) was added thereto, and the mixture was shaken for 2 hours. The resin was removed by filtration, and the filtrate was freeze-dried, to obtain the title compound (3.80 g).

The subject compound was hydrolyzed by the same condition as in Reference Example 4, and then the 4-phenylbutanol liberated therefrom was quantified by high performance liquid chromatography (HPLC), to thereby determine the binding ratio of the 4-phenylbutoxy group bound to the subject compound. The binding ratio was 62.3% with respect to the carboxyl groups of the polyglutamic acid.

Reference Example 8

Synthesis of Amide Conjugate of N-Acetylation Product of Block Copolymer of Monomethoxypolyethylene Glycol Having a Molecular Weight of about 12000 and Polyglutamic Acid Having a Polymerization Number of about 26, with L-Phenylalanine Benzyl Ester (about 30% with Respect to Carboxyl Groups of Polyglutamic Acid)

The N-acetylation product (1000 mg) of a block copolymer of monomethoxypolyethylene glycol having a molecular weight about 12000 and polyglutamic acid having a polymerization number of about 26 as described in Reference Example 1, L-phenylalanine benzyl ester hydrochloride (147 mg), and N,N-diisopropylethylamine (88 µL) were dissolved in N,N-dimethylformamide (25 mL), DMT-MM (167 mg) was added there to, and the mixture was stirred overnight at 40° C. The reaction liquid was cooled to room temperature, and then was added dropwise to a mixed solvent of diisopropyl ether-ethanol (4:1, 250 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex SOW (proton type, 4 mL) was added thereto, and the mixture was shaken at room temperature for 2 hours. The resin was removed by filtration, and the resin was washed with a 50% aqueous solution of acetonitrile. The resulting filtrate was concentrated under reduced pressure to a half the volume, and then was freeze-dried, to obtain the title compound (1070 mg).

The subject compound was hydrolyzed by the same condition as in Reference Example 4, and then the benzyl alcohol liberated therefrom was quantified by high performance liquid chromatography (HPLC) under the same conditions as in Reference Example 4, to thereby determine the binding ratio of the Phe-OBzl group bound to the subject compound via an amide linkage. The binding ratio was 30.8% with respect to the carboxyl groups of the polyglutamic acid.

Reference Example 9

Synthesis of Amide Conjugate of N-Acetylation Product of Block Copolymer of Monomethoxypolyethylene Glycol Having a Molecular Weight of about 12000 and Polyglutamic Acid Having a Polymerization Number of about 26, with L-Phenylalanine Benzyl Ester (about 55% with Respect to Carboxyl Groups of Polyglutamic Acid)

The N-acetylation product (596 mg) of a block copolymer of monomethoxypolyethylene glycol having a molecular weight about 12000 and polyglutamic acid having a polymerization number of about 26 as described in Reference Example 1, L-phenylalanine benzyl ester hydrochloride (161 mg), and N,N-diisopropylethylamine (96 µL) were dissolved in N,N-dimethylformamide (10 mL), DMT-MM (183 mg) was added there to, and the mixture was stirred overnight at 40° C. The reaction liquid was cooled to room temperature, and then was added dropwise to a mixed solvent of diisopropyl ether-ethanol (4:1, 100 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex SOW (proton type, 2 mL) was added thereto, and the mixture was shaken at room temperature for 2 hours. The resin was removed by filtration, and the resin was washed with a 50% aqueous solution of acetonitrile. The resulting filtrate was concentrated under reduced pressure to a half the volume, and then was freeze-dried, to obtain the title compound (630 mg).

The subject compound was hydrolyzed by the same condition as in Reference Example 4, and then the benzyl alcohol liberated therefrom was quantified by high performance liquid chromatography (HPLC) under the same conditions as in Reference Example 4, to thereby determine the binding ratio of the Phe-OBzl group bound to the subject compound via an amide linkage. The binding ratio was 56.8% with respect to the carboxyl groups of the polyglutamic acid.

Reference Example 10

Synthesis of Amide Conjugate of N-Acetylation Product of Block Copolymer of Monomethoxypolyethylene Glycol Having a Molecular Weight of about 12000 and Polyglutamic Acid Having a Polymerization Number of about 26, with L-Phenylalanine Benzyl Ester (about 60% with Respect to Carboxyl Groups of Polyglutamic Acid)

The N-acetylation product (2.32 g) of a block copolymer of monomethoxypolyethylene glycol having a molecular weight about 12000 and polyglutamic acid having a polymerization number of about 26 as described in Reference Example 3, L-phenylalanine benzyl ester hydrochloride (770 mg), and N,N-diisopropylethylamine (460 µL) were dissolved in N,N-dimethylformamide (40 mL), DMT-MM (877 mg) was added thereto, and the mixture was stirred overnight at 40° C. The reaction liquid was cooled to room temperature, and then was added dropwise to a mixed solvent of diisopropyl ether-ethanol (4:1, 450 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 10 mL) was added thereto, and the mixture was shaken at room temperature for 2 hours. The resin was removed by filtration, and the resin was washed with a 50% aqueous solution of acetonitrile. The resulting filtrate was concentrated under reduced pressure to a half the volume, and then was freeze-dried, to obtain the title compound (2.69 g).

The subject compound was hydrolyzed by the same condition as in Reference Example 4, and then the benzyl alcohol liberated therefrom was quantified by high performance liquid chromatography (HPLC) under the same conditions as in Reference Example 4, to thereby determine the binding ratio of the Phe-OBzl group bound to the subject compound via an amide linkage. The binding ratio was 60.4% with respect to the carboxyl groups of the polyglutamic acid.

Reference Example 11

Synthesis of Ester Conjugate of N-Acetylation Product of Block Copolymer of Monomethoxypolyethylene Glycol Having a Molecular Weight of about 12000 and Polyglutamic Acid Having a Polymerization Number of about 26, with 4-Phenylbutyl Bromide (about 50% with Respect To Carboxyl Groups of Polyglutamic Acid)

The N-acetylation product (290 mg) of a block copolymer of monomethoxypolyethylene glycol having a molecular weight about 12000 and polyglutamic acid having a polymerization number of about 26 as described in Reference Example 2, was dissolved in N,N-dimethylformamide (7.5 mL), 4-phenylbutyl bromide (64 mg) and 1,8-diazabicyclo[5.4.0]-7-undecene (DBU, 75 µL) were added thereto, and the mixture was stirred overnight at 40° C. The reaction liquid was cooled to room temperature, and then was added dropwise to a mixed solvent of diisopropyl ether-ethanol (4:1, 100 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 2 mL) was added thereto, and the mixture was shaken for 2 hours. The resin was removed by filtration, and the filtrate was freeze-dried, to obtain the title compound (305 mg).

The subject compound was hydrolyzed by the same condition as in Reference Example 4, and then the 4-phenylbutanol liberated therefrom was quantified by high performance liquid chromatography (HPLC), to thereby determine the binding ratio of the 4-phenylbutoxy group bound to the subject compound. The binding ratio was 50.4% with respect to the carboxyl groups of the polyglutamic acid.

Example 1

High Molecular Weight Derivative of Nucleic Acid Antimetabolite of Formula (1) in which R is Methyl Group, A is Acetyl Group, Average Value of m is 26, Average Value of n is 272, X is Gemcitabine Residue, Hydroxyl Group, L-Phenylalanine Benzyl Ester Residue and Isopropylaminocarbonylisopropylamino Group (Compound 1 in Table 1)

To the compound synthesized in Reference Example 4 (480 mg) and gemcitabine hydrochloride (125 mg), N,N-dimethylformamide (10 mL) and N,N-diisopropylethylamine (73 µL) were added, and the mixture was stirred at 40° C. After dissolving the compounds, 4-dimethylaminopyridine (10.2 mg) and diisopropylcarbodiimide (131 µL) were added thereto, and the resulting mixture was stirred overnight at 40° C. The reaction liquid was cooled to room temperature, and then was added dropwise to a mixed solvent of diisopropyl ether-ethanol (4:1, 100 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 2 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half the volume, and then was freeze-dried, to obtain the title compound (453 mg).

The subject compound was hydrolyzed, and then the gemcitabine liberated therefrom was quantified by high performance liquid chromatography (HPLC) to determine the gemcitabine content in the subject compound, which was 8.4% (w/w) in terms of gemcitabine hydrochloride. The compound of the present invention was also analyzed by HPLC, and the content of free gemcitabine was 0.2% or less.

Method of Hydrolysis

The title compound (11.36 mg) was dissolved in methanol (1.0 mL), a 0.5 M aqueous solution of sodium hydroxide (1.0 mL) was added thereto, and the mixture was stirred for 1 hour at 40° C. The mixture was neutralized with acetic acid, and then was diluted with distilled water, to obtain precisely 10 mL of the solution.

Analysis Conditions for HPLC (Analysis of Gemcitabine)

Column: YMC Hydrosphere, 4.6φ×250 mm;

Column temperature: 40° C.;

Eluent liquid A: 1% aqueous solution of phosphoric acid, liquid B: acetonitrile;

Gradient: liquid B % (time, minutes) 0(0), 0(5), 80(25) 80(35), stop (35.01);

Flow rate: 1 mL/min;

Detector (detection wavelength): UV (210 nm)

Furthermore, the molar ratio of the isopropylaminocarbonylisopropylamino group with respect to gemcitabine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.47.

Example 2

High Molecular Weight Derivative of Nucleic Acid Antimetabolite of Formula (1) in which R is Methyl Group, A is Acetyl Group, Average Value of m is 26, Average Value of n is 272, X is Gemcitabine Residue, Hydroxyl Group, L-Phenylalanine Benzyl Ester Residue and Isopropylaminocarbonylisopropylamino Group (Compound 2 in Table 1)

To the compound synthesized in Reference Example 5 (567 mg) and gemcitabine hydrochloride (92 mg), N,N-dimethylformamide (15 mL) and N,N-diisopropylethylamine (54 µL) were added, and the mixture was stirred at 40° C. After dissolving the compounds, 4-dimethylaminopyridine (7.5 mg) and diisopropylcarbodiimide (96 µL) were added thereto, and the resulting mixture was stirred overnight at 40° C. The reaction liquid was cooled to room temperature, and then was added dropwise to a mixed solvent of diisopropyl ether-ethanol (4:1, 200 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 2 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half the volume, and then was freeze-dried, to obtain the title compound (539 mg).

The subject compound was hydrolyzed by the same condition as in Example 1, and then the gemcitabine liberated therefrom was quantified by high performance liquid chromatography (HPLC) under the same conditions as in Example 1, to determine the gemcitabine content in the subject compound, which was 4.0% (w/w) in terms of gemcitabine hydrochloride. The compound of the present invention was also analyzed by HPLC, and the content of free gemcitabine was 0.2% or less.

Example 3

High Molecular Weight Derivative of Nucleic Acid Antimetabolite of Formula (1) in which R is Methyl Group, A is Acetyl Group, Average Value of m is 26, Average Value of n is 272, X is Gemcitabine Residue, Hydroxyl Group, 4-Phenylbutyl Alcohol Residue and Isopropylaminocarbonylisopropylamino Group (Compound 3 in Table 1)

To the compound synthesized in Reference Example 6 (1027 mg) and gemcitabine hydrochloride (285 mg), N,N-dimethylformamide (20 mL) and N,N-diisopropylethylamine (165 µL) were added, and the mixture was stirred at 40° C. After dissolving the compounds, 4-dimethylaminopyridine (23.2 mg) and diisopropylcarbodiimide (297 µL) were added thereto, and the resulting mixture was stirred overnight at 40° C. The reaction liquid was cooled to room temperature, and then was added dropwise to a mixed solvent of diisopropyl ether-ethanol (4:1, 200 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 4 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half the volume, and then was freeze-dried, to obtain the title compound (1070 mg).

The subject compound was hydrolyzed by the same condition as in Example 1, and then the gemcitabine liberated therefrom was quantified by high performance liquid chromatography (HPLC) under the same conditions as in Example 1, to determine the gemcitabine content in the subject compound, which was 9.1% (w/w) in terms of gemcitabine hydrochloride. The compound of the present invention was also analyzed by HPLC, and the content of free gemcitabine was 0.2% or less.

Furthermore, the molar ratio of the isopropylaminocarbonylisopropylamino group with respect to gemcitabine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.55.

Example 4

High Molecular Weight Derivative of Nucleic Acid Antimetabolite of Formula (1) in which R is Methyl Group, A is Acetyl Group, Average Value of m is 26, Average Value of n is 272, X is Gemcitabine Residue, Hydroxyl Group, 4-Phenylbutyl Alcohol Residue and Isopropylaminocarbonylisopropylamino Group (Compound 4 in Table 1)

To the compound synthesized in Reference Example 7 (1650 mg) and gemcitabine hydrochloride (300 mg), N,N-dimethylformamide (30 mL) and N,N-diisopropylethylamine (174 µL) were added, and the mixture was stirred at 40° C. After dissolving the compounds, 4-dimethylaminopyridine (24.4 mg) and diisopropylcarbodiimide (313 µL) were added thereto, and the resulting mixture was stirred overnight at 40° C. The reaction liquid was cooled to room temperature, and then was added dropwise to a mixed solvent of diisopropyl ether-ethanol (4:1, 300 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 6 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half the volume, and then was freeze-dried, to obtain the title compound (1678 mg).

The subject compound was hydrolyzed by the same condition as in Example 1, and then the gemcitabine liberated therefrom was quantified by high performance liquid chromatography (HPLC) under the same conditions as in Example 1, to determine the gemcitabine content in the subject compound, which was 4.9% (w/w) in terms of gemcitabine hydrochloride. The compound of the present invention was also analyzed by HPLC, and the content of free gemcitabine was 0.2% or less.

Furthermore, the molar ratio of the isopropylaminocarbonylisopropylamino group with respect to gemcitabine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.72.

Example 5

High Molecular Weight Derivative of Nucleic Acid Antimetabolite of Formula (1) in which R is Methyl Group, A is Acetyl Group, Average Value of m is 26, Average Value of 272, X is Doxifluridine Residue, Hydroxyl Group, L-Phenylalanine Benzyl Ester Residue and Isopropylaminocarbonylisopropylamino Group (Compound 5 in Table 1)

To the compound synthesized in Reference Example 8 (476 mg) and doxifluridine (123 mg), N,N-dimethylformamide (10 mL) was added, and the mixture was stirred at 40° C. After dissolving the compounds, 4-dimethylaminopyridine (12.2 mg) and diisopropylcarbodiimide (157 µL) were added thereto, and the resulting mixture was stirred overnight at 40° C. The reaction liquid was cooled to room temperature, and then was added dropwise to a mixed solvent of diisopropyl ether-ethanol (4:1, 150 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 3 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half the volume, and then was freeze-dried, to obtain the title compound (485 mg).

The subject compound was hydrolyzed by the same condition as in Example 1, and then the doxifluridine liberated therefrom was quantified by high performance liquid chromatography (HPLC) under the same conditions as in Example 1, to determine the doxifluridine content in the subject compound, which was 9.0% (w/w) in terms of doxifluridine. The compound of the present invention was also analyzed by HPLC, and the content of free doxifluridine was 0.2% or less.

Furthermore, the molar ratio of the isopropylaminocarbonylisopropylamino group with respect to doxifluridine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.76.

Example 6

High Molecular Weight Derivative of Nucleic Acid Antimetabolite of Formula (1) in which R is Methyl Group, A is Acetyl Group, Average Value of m is 26, Average Value of n is 272, X is Gemcitabine Residue, Hydroxyl Group, L-Phenylalanine Benzyl Ester Residue and Isopropylaminocarbonylisopropylamino Group (Compound 6 in Table 1)

To the compound synthesized in Reference Example 9 (100 mg) and gemcitabine hydrochloride (21 mg), N,N-dimethylformamide (2.5 mL) and N,N-diisopropylethylamine (12.2 µL) were added, and the mixture was stirred at 40° C. After dissolving the compounds, 4-dimethylaminopyridine (1.7 mg) and diisopropylcarbodiimide (21.9 µL) were added thereto, and the resulting mixture was stirred overnight at 40° C. The reaction liquid was cooled to room temperature, and then was added dropwise to a mixed solvent of diisopropyl ether-ethanol (4:1, 50 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 1 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half the volume, and then was freeze-dried, to obtain the title compound (63 mg).

The subject compound was hydrolyzed by the same condition as in Example 1, and then the gemcitabine liberated therefrom was quantified by high performance liquid chromatography (HPLC) under the same conditions as in Example 1, to determine the gemcitabine content in the subject compound, which was 6.6% (w/w) in terms of gemcitabine hydrochloride. The compound of the present invention was also analyzed by HPLC, and the content of free gemcitabine was 0.2% or less.

Example 7

High Molecular Weight Derivative of Nucleic Acid Antimetabolite of Formula (1) in which R is Methyl Group, A is Acetyl Group, Average Value of m is 26, Average Value of n is 272, X is Gemcitabine Residue, Hydroxyl Group, L-Phenylalanine Benzyl Ester Residue and Isopropylaminocarbonylisopropylamino Group (Compound 7 in Table 1)

To the compound synthesized in Reference Example 10 (2.50 g) and gemcitabine hydrochloride (415 mg), N,N-dimethylformamide (45 mL) and N,N-diisopropylethylamine (241 µL) were added, and the mixture was stirred at 40° C. After dissolving the compounds, 4-dimethylaminopyridine (33.8 mg) and diisopropylcarbodiimide (433 µL) were added thereto, and the resulting mixture was stirred overnight at 40° C. The reaction liquid was cooled to room temperature, and then was added dropwise to a mixed solvent of diisopropyl ether-ethanol (4:1, 500 mL). After stirring the mixture for 30 minutes, a precipitate separated out therefrom was collected by filtration, and was washed with a mixed solvent of diisopropyl ether-ethanol (4:1). The obtained product was dissolved in a 70% aqueous solution of acetonitrile, and the solution was dialyzed with distilled water (2 L×3) using a dialysis membrane (molecular weight cut-off: 12000 to 14000). The dialyzed solution was freeze-dried, to obtain the title compound (2.45 g).

The subject compound was hydrolyzed by the same condition as in Example 1, and then the gemcitabine liberated therefrom was quantified by high performance liquid chromatography (HPLC) under the same conditions as in Example 1, to determine the gemcitabine content in the subject compound, which was 6.12% (w/w) in terms of gemcitabine hydrochloride. The compound of the present invention was also analyzed by HPLC, and the content of free gemcitabine was 0.2% or less.

Furthermore, the molar ratio of the isopropylaminocarbonylisopropylamino group with respect to gemcitabine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.65.

Example 8

High Molecular Weight Derivative of Nucleic Acid Antimetabolite of Formula (1) in which R is Methyl Group, A is Acetyl Group, Average Value of m is 26, Average Value of n is 272, X is Gemcitabine Residue, Hydroxyl Group, 4-phenylbutyl Alcohol Residue and Isopropylaminocarbonylisopropylamino Group (Compound 8 in Table 1)

To the compound synthesized in Reference Example 11 (305 mg) and gemcitabine hydrochloride (71 mg), N,N-dimethylformamide (7.5 mL) and N,N-diisopropylethylamine (41 µL) were added, and the mixture was stirred at 40° C. After dissolving the compounds, 4-dimethylaminopyridine (5.8 mg) and diisopropylcarbodiimide (74 µL) were added thereto, and the resulting mixture was stirred overnight at 40° C. The reaction liquid was cooled to room temperature, and then was added dropwise to a mixed solvent of diisopropyl ether-ethanol (4:1, 100 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 2.5 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half the volume, and then was freeze-dried, to obtain the title compound (292 mg).

The subject compound was hydrolyzed by the same condition as in Example 1, and then the gemcitabine liberated therefrom was quantified by high performance liquid chromatography (HPLC) under the same conditions as in Example 1, to determine the gemcitabine content in the subject compound, which was 7.9% (w/w) in terms of gemcitabine hydrochloride. The compound of the present invention was also analyzed by HPLC, and the content of free gemcitabine was 0.2% or less.

Test Example 1

Drug Release Test in the Absence of Enzyme

The compound of Example 1 (indicated as Compound 1 in FIG. 1), the compound of Example 2 (indicated as Compound 2 in FIG. 1), the compound of Example 4 (indicated as Compound 4 in FIG. 1), or the compound of Example 5 (indicated as Compound 5 in FIG. 1) was dissolved in phosphate buffered physiological saline (pH 7.4) to a concentration of 1.0 mg/mL, and the solution was left to stand at a constant temperature of 37° C. The amount of released gemcitabine or doxifluridine was measured over time by HPLC, and the ratio of the amount of released gemcitabine or doxifluridine with respect to the total amount of gemcitabine or doxifluridine in the respective compounds used was determined. The results are presented in FIG. 1. The compounds of the present invention were found to release the drugs slowly in a manner not dependent on enzymes.

Test Example 2

Drug Release in Mouse Blood Plasma

The compound of Example 4 (indicated as Compound 4 in FIG. 2) or the compound of Example 5 (indicated as Compound 5 in FIG. 2) was dissolved in phosphate buffered physiological saline (pH 7.4), and subsequently blood plasma collected and prepared from mice was added thereto in a four-fold amount (v/v), and the solution was left to stand at a constant temperature of 37° C. 50 µL each of the solution was sampled over time, and was diluted with a 50% aqueous solution of methanol (450 µL). The dilution was subjected to deproteinization with a membrane filter (pore size 0.45 µm), and then the amount of gemcitabine released from the compound of the present invention was measured over time by HPLC, to determine the ratio of the amount of released gemcitabine with respect to the total amount of gemcitabine in the respective compounds of the present invention. The results are presented in FIG. 2.

When the results of Test Example 1 and Test Example 2 are compared, it seems that, in the mouse blood plasma, the compounds of the present invention have higher drug release rates as compared to the case in the absence of enzymes, but the compounds remain for a long time as high molecular weight derivatives and keep releasing the drugs even in the presence of the plasma.

Test Example 3

Antitumor Effect Against Tumor-Bearing Mouse (1)

Tumor of mouse colon cancer, Colon26, maintained by serial subcutaneous subculture in mice, was minced into about 2-mm square blocks, and the blocks were transplanted subcutaneously on the dorsal part of a mouse using a trocar. On the 7$^{th}$ day after tumor transplantation, the compound of Example 1 (indicated as Compound 1 in Table 2) and the compound of Example 2 (indicated as Compound 2 in Table 2), respectively dissolved in physiological saline, and gemcitabine hydrochloride as a control drug dissolved in a 5% glucose injection solution were respectively administered once intravenously at the doses indicated in Table 2. The tumor volumes on the day of initiation of administration and on the 7$^{th}$ day after the initiation of administration were calculated by the following equation, and the relative tumor volumes on the day of initiation of administration and on the 7th day after the initiation of administration were determined. The results are presented in Table 2.

$$\text{Tumor volume(mm}^3) = \frac{[\text{Major axis of tumor(mm)}] \times [\text{Minor axis of tumor(mm)}] \times [\text{Minor axis of tumor(mm)}]}{2}$$

TABLE 2

| Drug | Dose (in terms of gemcitabine hydrochloride) (mg/kg) | Relative tumor volume* |
|---|---|---|
| Untreated | 0 | 10.5 ± 5.0 |
| Compound 1 | 80 | 0.2 ± 0.1 |
|  | 40 | 3.5 ± 0.7 |
| Compound 2 | 80 | 0.3 ± 0.1 |
|  | 40 | 8.6 ± 3.8 |
| Control drug | 200 | 3.4 ± 0.6 |
|  | 100 | 3.9 ± 0.5 |

*Average relative tumor volume (average ± SD) on the 7th day after the initiation of administration, assuming that the tumor volume on the day of initiation of drug administration is 1.0

From these results, it is clear that when compared with the control drug, gemcitabine hydrochloride, the compounds of the present invention have equal or superior antitumor effects at lower doses.

Test Example 4

Antitumor Effect Against Tumor-Bearing Mouse (2)

Tumor of mouse colon cancer, Colon26, maintained by serial subcutaneous subculture in mice, was minced into about 2-mm square blocks, and the blocks were transplanted subcutaneously on the dorsal part of a mouse. On the 7th day after tumor transplantation, the compound of Example 3 (indicated as Compound 3 in Table 3) and the compound of Example 4 (indicated as Compound 4 in Table 3), respectively dissolved in physiological saline, and gemcitabine hydrochloride as a control drug dissolved in a 5% glucose injection solution were respectively administered once intravenously at the doses indicated in Table 3. The tumor volumes on the day of initiation of administration and on the 8th day after the initiation of administration were calculated in the same manner as in Test Example 3, and the relative tumor volumes on the day of initiation of administration and on the 8th day after the initiation of administration were determined. The results are presented in Table 3.

TABLE 3

| Drug | Dose (in terms of gemcitabine hydrochloride) (mg/kg) | Relative tumor volume* |
|---|---|---|
| Untreated | 0 | 10.3 ± 2.9 |
| Compound 3 | 60 | 0.4 ± 0.5 |
|  | 40 | 5.1 ± 0.4 |
| Compound 4 | 60 | 0.7 ± 0.5 |
|  | 40 | 5.4 ± 1.3 |
| Control drug | 200 | 4.8 ± 1.7 |
|  | 40 | 5.3 ± 1.1 |

*Average relative tumor volume (average ± SD) on the 8th day after the initiation of administration, assuming that the tumor volume on the day of initiation of drug administration is 1.0

From these results, it is clear that when compared with the control drug, gemcitabine hydrochloride, the compounds of the present invention have equal or superior antitumor effects at lower doses.

Figure 1:
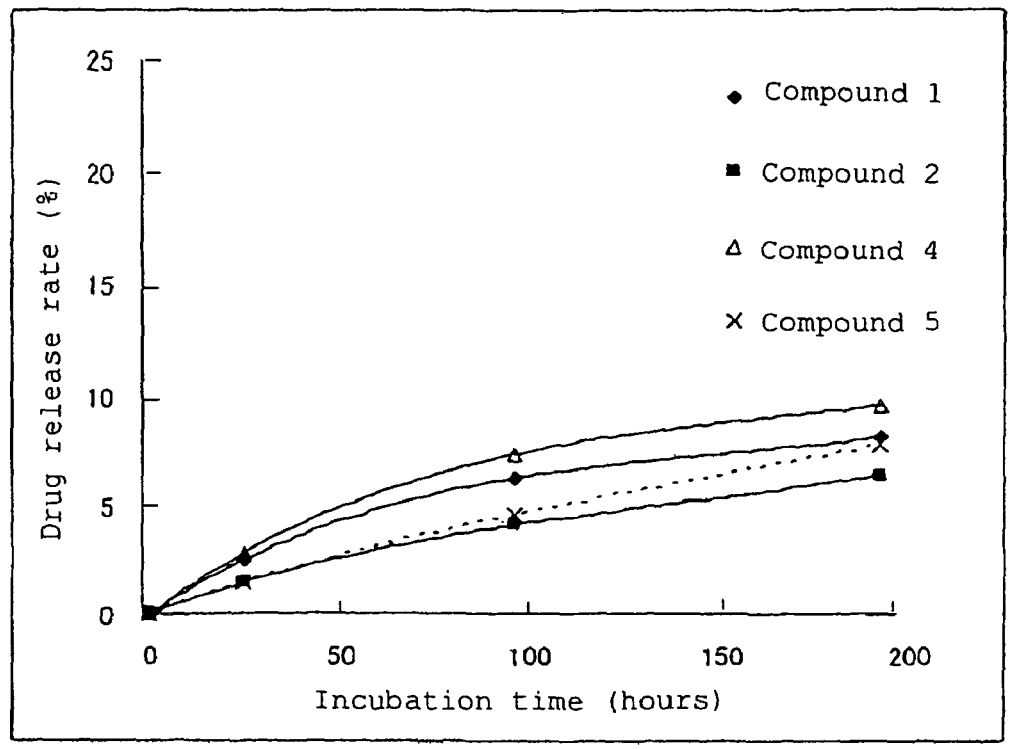
FIG. 1 shows the changes in drug release over time in the absence of enzymes. Symbol ♦ represents Compound 1, ■ represents Compound 2, ▲ represents Compound 4, and x represents Compound 5.
Figure 2:
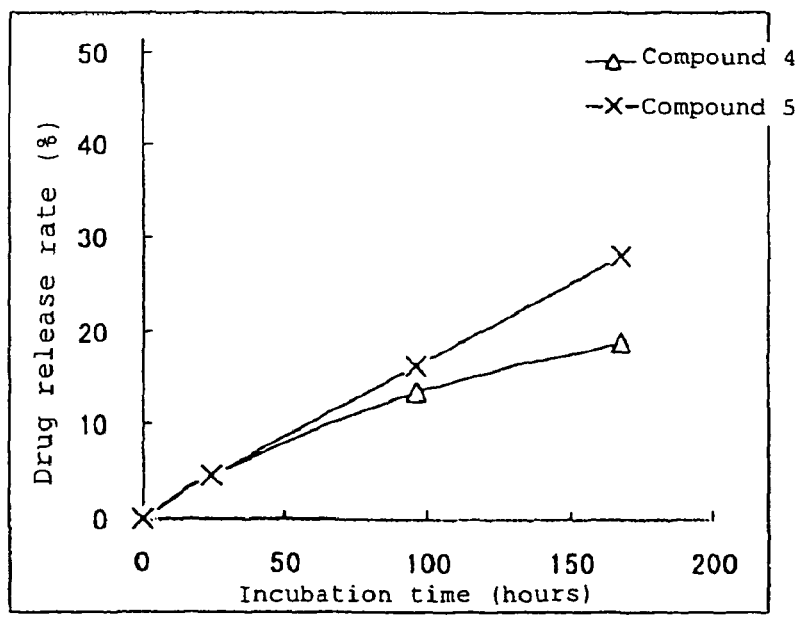
FIG. 2 shows the changes in drug release over time in the mouse blood plasma. Symbol Δ represents Compound 4, and x represents Compound 5.

The invention claimed is:

1. A high molecular weight derivative of a nucleic acid antimetabolite, in which a carboxyl group in the side chain of a high molecular weight compound comprising a polyethylene glycol moiety and a polymer moiety having a carboxyl group in the side chain is linked to a hydroxyl group of a nucleic acid antimetabolite via an ester linkage, wherein said high molecular weight derivative of a nucleic acid antimetabolite is represented by the following formula (1):

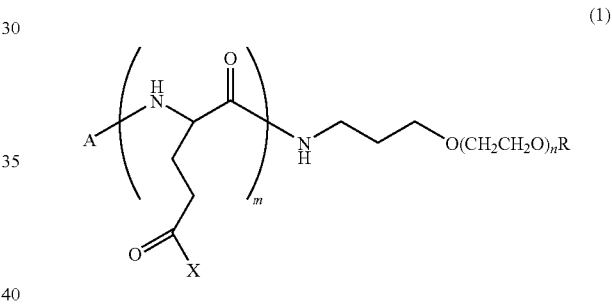

wherein R represents a hydrogen atom or a C1-C6 alkyl group;
A represents a hydrogen atom, a C1-C6 acyl group or a C1-C6 alkoxycarbonyl group; m represents from 3 to 200 as an average value; n represents from 5 to 2000 as an average value; and X represents a group selected from the group consisting of a nucleic acid antimetabolite residue, a hydroxyl group, a hydrophobic substituent, and —N(R1)CONH(R2) wherein R1 and R2 may be identical or different, and are each a C1-C6 alkyl group which may be substituted with a teritary amino group, X includes a nucleic acid antimetabolite residue and —N(R1)CONH(R2), and the nucleic acid antimetabolite residue is any one of the nucleic acid antimetabolite residues represented by the following formula (2):

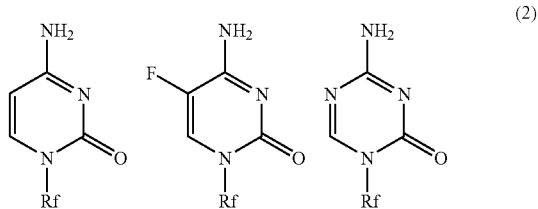

-continued

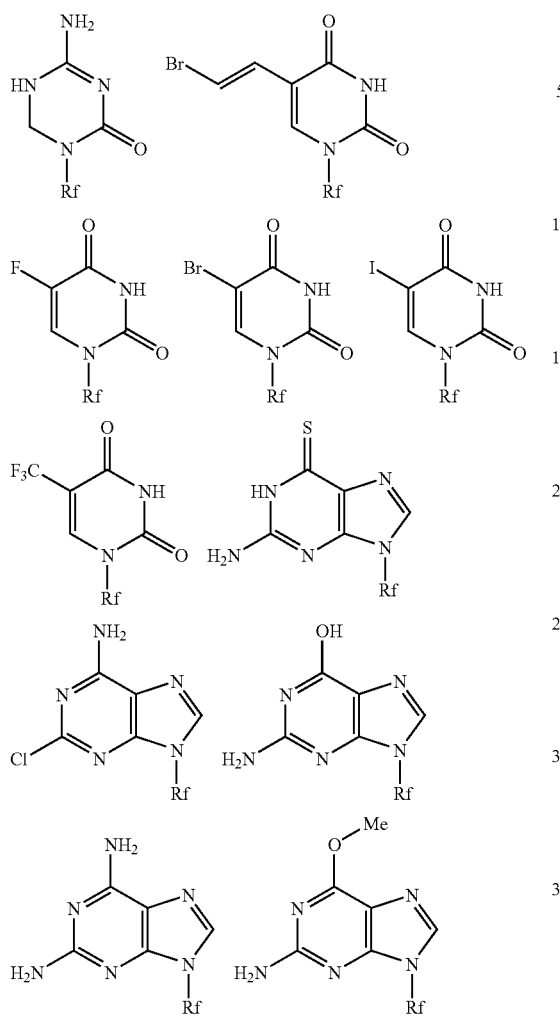

wherein —Rf represents a group selected from the group of substituents of formula (3):

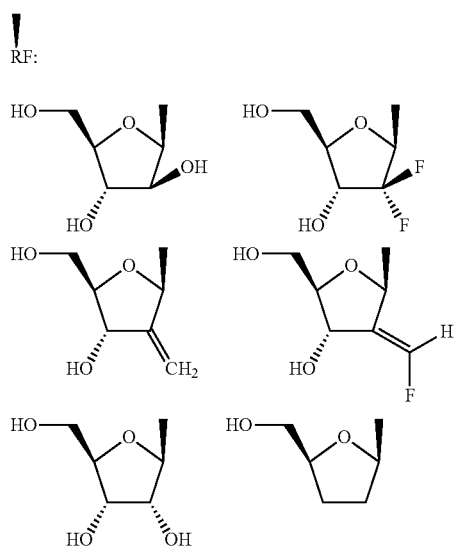
(3)

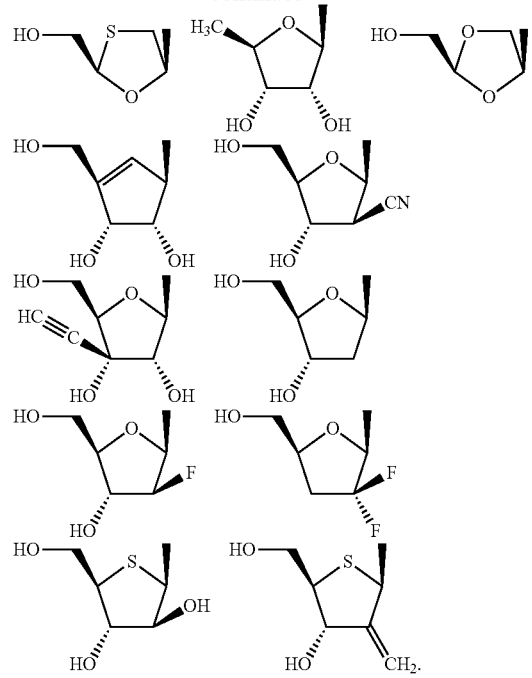

2. The high molecular weight derivative of a nucleic acid antimetabolite according to claim 1, wherein, among m units, 5 to 95% have a nucleic acid antimetabolite residue for X, 0 to 95% have a hydroxyl group for X, 0 to 80% have a hydrophobic substituent for X, and 5 to 80% have —N(R1)CONH(R2) for X.

3. The high molecular weight derivative of a nucleic acid antimetabolite according to claim 1, wherein, among m units, 5 to 70% have a nucleic acid antimetabolite residue for X, 5 to 70% have a hydroxyl group for X, 20 to 70% have a hydrophobic substituent for X, and 5 to 70% have —N(R1)CONH(R2) for X.

4. The high molecular weight derivative of a nucleic acid antimetabolite according to claim 1, wherein R is a C1-C4 alkyl group, A is a C2-C4 acyl group, m is from 5 to 100 as an average value, n is from 50 to 1000 as an average value.

5. The high molecular weight derivative of a nucleic acid antimetabolite according to claim 4, wherein R is a methyl group, A is an acetyl group, m is from 10 to 60 as an average value, n is from 100 to 300 as an average value, and the nucleic acid antimetabolite residue is a residue of gemcitabine or doxifluridine.

6. The high molecular weight derivative of a nucleic acid antimetabolite according to claim 1, wherein the hydrophobic substituent is an α-amino acid derivative represented by formula (4):

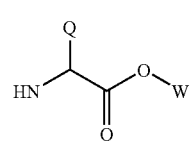
(4)

wherein Q represents the side chain of a neutral amino acid; and

W represents a C1-C6 alkyl group or a benzyl group.

7. The high molecular weight derivative of a nucleic acid antimetabolite according to claim 6, wherein Q is an isopropyl group or a benzyl group, and W is a benzyl group.

8. The high molecular weight derivative of a nucleic acid antimetabolite according to claim 1, wherein the hydrophobic substituent is a group represented by formula (5):

wherein T represents a C1-C6 alkyl group which may be substituted with a phenyl group.

9. The high molecular weight derivative of a nucleic acid antimetabolite according to claim 8, wherein T is a benzyl group, a 3-phenylpropyl group, a 4-phenylbutyl group or a 5-phenylpentyl group.

10. The high molecular weight derivative of a nucleic acid antimetabolite according to claim 1, wherein R is a methyl group, A is an acetyl group, m is from 10 to 60 as an average value, n is from 100 to 300 as an average value, the nucleic acid antimetabolite residue is a gemcitabine residue, the hydrophobic substituent is a 4-phenylbutoxy group or a (1-benzyloxycarbonyl-2-phenyl)ethylamino group, and —N(R1)CONH(R2) is an isopropylaminocarbonylisopropylamino group.

11. A high molecular weight derivative of a nucleic acid antimetabolite, obtained by linking a carboxyl group in the side chain of a high molecular weight compound comprising a polyethylene glycol moiety and a polymer moiety having a carboxyl group in the side chain, with a nucleic acid antimetabolite via an ester linkage, using a carbodiimide-based condensing agent in an organic solvent.

12. An antitumor agent comprising the high molecular weight derivative of a nucleic acid antimetabolite according to claim 1 as an active ingredient.

13. An antiviral agent comprising the high molecular weight derivative of a nucleic acid antimetabolite according to claim 1 as an active ingredient.

* * * * *